(12) United States Patent
Carter et al.

(10) Patent No.: US 8,722,874 B2
(45) Date of Patent: May 13, 2014

(54) DOUBLE-STRANDED RIBONUCLEIC ACIDS WITH RUGGED PHYSICO-CHEMICAL STRUCTURE AND HIGHLY SPECIFIC BIOLOGIC ACTIVITY

(75) Inventors: William A. Carter, Birchrunville, PA (US); David R. Strayer, Bryn Mawr, PA (US)

(73) Assignee: HEMISPHERx BioPharma, Inc., Philadelphia, PA (US)

( * ) Notice: Subject to any disclaimer, the term of this patent is extended or adjusted under 35 U.S.C. 154(b) by 0 days.

(21) Appl. No.: 13/077,742

(22) Filed: Mar. 31, 2011

(65) Prior Publication Data

US 2012/0009206 A1   Jan. 12, 2012

Related U.S. Application Data

(63) Continuation-in-part of application No. PCT/US2010/002970, filed on Nov. 12, 2010, which is a continuation-in-part of application No. 12/591,270, filed on Nov. 13, 2009, which is a continuation-in-part of application No. PCT/US2009/005797, filed on Oct. 23, 2009.

(60) Provisional application No. 61/193,030, filed on Oct. 23, 2008.

(51) Int. Cl.
*C07H 21/04* (2006.01)
*C07H 21/02* (2006.01)

(52) U.S. Cl.
USPC ........................................ 536/24.5; 536/23.1

(58) Field of Classification Search
None
See application file for complete search history.

(56) References Cited

U.S. PATENT DOCUMENTS

RE39,071 E    4/2006  Baker et al.
2008/0317811 A1  12/2008  Andre et al.

FOREIGN PATENT DOCUMENTS

| WO | WO 2008/109083 | 9/2008 |
|---|---|---|
| WO | WO 2009/102496 | 8/2009 |
| WO | WO 2010/047835 | 4/2010 |
| WO | WO 2011/059505 | 5/2011 |

OTHER PUBLICATIONS

Notification Concerning Transmittal of International Preliminary Report on Patentability (Chapter 1 of the Patent Cooperation Treaty) dated Apr. 26, 2011 issued in connection with PCT/US2009/005797.
Notification of Transmittal of the International Search Report and the Written Opinion of the International Searching Authority, or the Declaration dated Aug. 2, 2011 issued in connection with PCT/US2010/002970.
Miller et al, "Thermodynamic analysis of 5' and 3' single- and 3' double-nucleotide overhangs neighboring wobble terminal base pairs", Nucleic Acids Research 36(17):5652-5659 (2008).
Jasani et al, "Ampligen: A potential toll-like 3 receptor adjuvant for immunotherapy of cancer", Vaccine 27:3401-3404 (2009).

*Primary Examiner* — Amy Bowman
(74) *Attorney, Agent, or Firm* — Nixon & Vanderhye P.C.

(57) ABSTRACT

A novel form of Rugged dsRNA with a unique composition and physical characteristics was identified with high specificity of binding to TLR3, which conveys an important range of therapeutic opportunities. Unlike the previous known antiviral Ampligen® (poly I, poly C12,U) the new and improved form (poly I, poly $C_{30}$,U) has a reduced tendency to form branched dsRNA which results in increased bioactivity due to an increased ability to bind TLR3 receptor. Pharmaceutical formulations containing the new nucleic acid as active ingredients and methods of treatment are also provided. The invention also provides a description of the physicochemical properties of this novel form of Rugged dsRNA and a method for its preparation in substantially pure form. DsRNAs acting thru TLR3 receptor activation are potent antiviral compounds as well as anticancer agents; also through secondary immunomodulation they can enhance the bioactivity of vaccines and also treat autoimmune disorders.

4 Claims, 24 Drawing Sheets

Poly C12U Lot: 806303801 (7.0S)

Standard Measurements - Ampligen v. Poly I:C

Melting Curves - Ampligen v. Poly A:U

Formulated Ampligen Lot 010205-7 (Poly I + Poly C10U)

Rugged dsRNA Molecular Weight: 30,000 to 300,000 Daltons

Unimproved Ampligen®

FIGURE 27
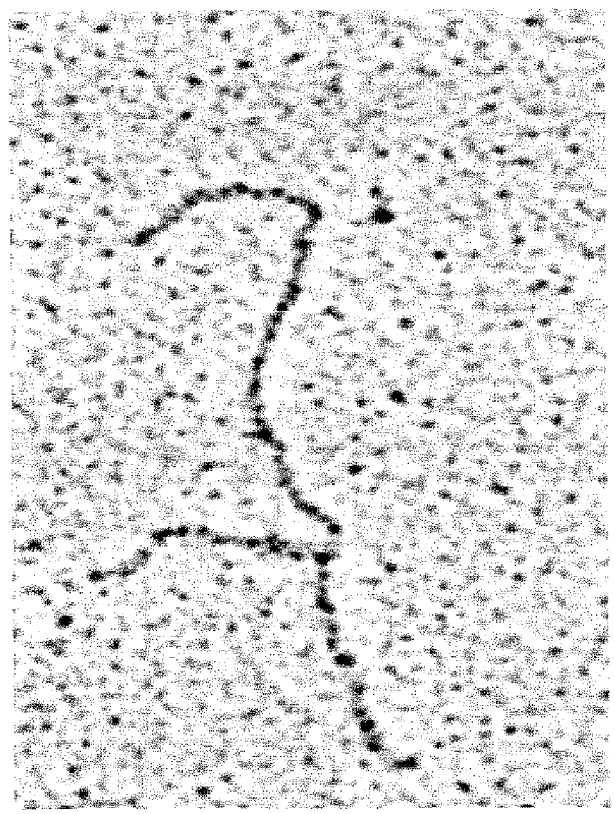
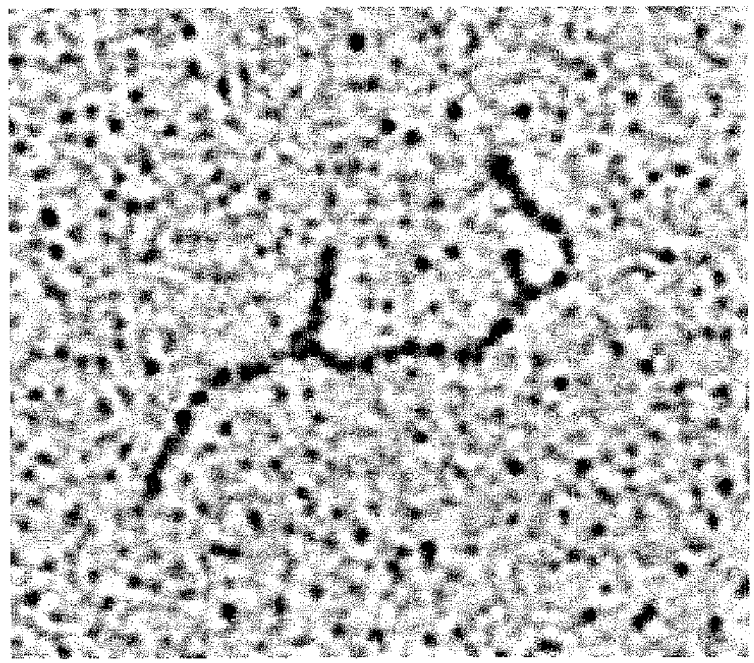
Unimproved Ampligen®

Unimproved Ampligen®

FIGURE 29
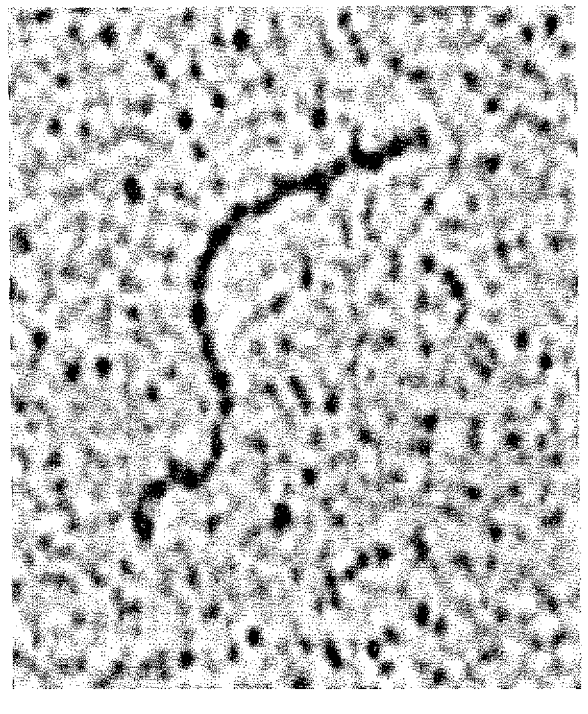
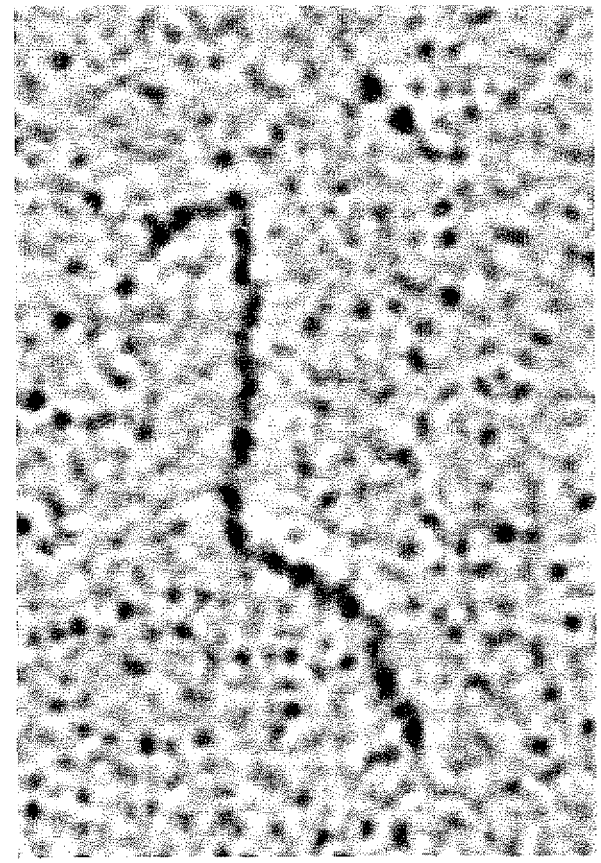
Rugged dsRNA

DOUBLE-STRANDED RIBONUCLEIC ACIDS WITH RUGGED PHYSICO-CHEMICAL STRUCTURE AND HIGHLY SPECIFIC BIOLOGIC ACTIVITY

CROSS REFERENCE TO RELATED APPLICATIONS

This application is a continuation-in-part of PCT/US2010/002970, filed Nov. 12, 2010, which is a continuation-in-part of U.S. application Ser. No. 12/591,270, filed Nov. 13, 2009, which is a continuation-in-part of International Application No. PCT/US2009/005797, filed Oct. 23, 2009 which claims priority benefit of U.S. provisional application, Ser. No. 61/193,030, filed Oct. 23, 2008 the disclosures of all of which are hereby incorporated by reference.

FIELD OF THE INVENTION

The invention relates to our discovery of a novel and improved double-stranded ribonucleic acid (dsRNA) having specific biological activities, which includes acting as a selective agonist for activation of Toll-like receptor 3 (TLR3). Its smaller and "rugged" molecular structure as measured by physico-chemical techniques is resistant to molecular unfolding (i.e., denaturation) and branching. This structure appears to be responsible for increased efficacy of dsRNA in therapeutic applications and improved biological activity (e.g., used as an immunoregulatory agent).

BACKGROUND OF THE INVENTION

Ampligen® poly(I):poly($C_{12}U$) was developed as a synthetic double-stranded ribonucleic acid (dsRNA) for therapeutic applications based on an understanding of both the beneficial and adverse effects induced by poly(I):poly(C) on the physiology of a subject. Acting on the hypothesis that the nucleotide sequence requirements for beneficial and adverse effects are different, poly(I):poly($C_{12}U$) was developed by us to preserve the beneficial aspects of dsRNA without the adverse effects of poly(I):poly(C) by modifying the latter's structure with the occasional introduction of uridylate into the poly(C) strand to produce duplexes containing specifically-configured regions which are not base paired (i.e., "mismatched") at the position of the modification. These regions accelerate dsRNA hydrolysis and lessen toxicity (Greene, 1984). On the other hand, the ability to induce interferon synthesis was retained as long as the modified dsRNA persisted for a half life of at least five minutes and the frequency of random insertion into the poly(ribocytidylic acid) strand was not greater than each 0.5 to 1.0 helical turn of perfectly base-paired dsRNA (Brodsky, 1987).

While poly(I):poly($C_{12}U$) is stable in solution, it is susceptible to hydrolysis like all other conventional nucleic acids. The hydrolysis is highly dependent on nucleic acid structure, as well as on the presence of nuclease and divalent cations, pH, and temperature. RNA is more susceptible to hydrolysis than DNA because of the 2'-OH group present in the former that facilitates hydrolysis. Moreover, poly(I):poly($C_{12}U$) was designed to degrade more rapidly than other dsRNA in a nuclease-containing environment, such as blood and other tissue fluids. Nucleic acids are initially stable in physiological salt buffers at room temperature, but gradually begin to degrade with time. This hydrolysis rate is temperature dependent, increasing greatly at higher temperatures.

Properties of poly(I):poly($C_{12}U$) are characterized by physico-chemical assays as shown in Table 1. Circular dichroism (CD) (e.g., ellipticity, melting behavior) is used to characterize the double-helical RNA structure, which is critical to potency. Briefly, Toll-like receptor 3 (TLR3) is activated by dsRNA (Alexopoulou, 2001), which leads to a host defense recruitment sequence, ultimately producing type I interferons (Schroeder, 2005). Initiation of interferon production by dsRNA binding to TLR3 requires RNA helical structure (Bell, 2006). Although X-ray diffraction and NMR alone are the definitive techniques to determine RNA second-order structure, CD measurement with a combination of scanning and thermal stress modes also can provide precise characterization of the critical double-helical structure. Indeed, minor changes in second-order structure of polynucleotides have been measured by CD (Gray, 1995), including the effects of ligand binding (Sumita, 2005).

TABLE 1

Biological Activity and Measured Attributes.

| Measured Property | Identity Attribute | Activity Attribute |
|---|---|---|
| Conformation: Second Degree | | |
| CD: Ellipticity | Double-Stranded RNA: integrity of helix | binding to TLR3 |
| CD: Melting Behavior: Melting Point ½ Width | Double-Stranded RNA: integrity and uniformity of helix | binding to TLR3 binding to TLR3 |
| Composition and Size | | |
| Maximum Size | No. of Repeat Units | Tendency to form Branched Structure |
| C:U Ratio | identity | Tendency to form Branched Structure |

Therefore, circular dichroism can be employed to characterize the therapeutic potency of specifically-configured dsRNAs including poly(I):poly($C_{12}U$) and a new improved dsRNA called Rugged dsRNA.

A problem of Ampligen®, poly (I): poly (C12U), is its lower than expected biological activity traced to a branching structure. Our invention is the unexpected discovery of a new family of improved dsRNAs having a specific physico-chemical structure and highly specific biological activities, which includes acting as a selective agonist for TLR3. This invention relates to the discovery of this new and improved version of dsRNA with a superior biological and therapeutic profile. The new and improved dsRNA, called Rugged dsRNA, can be present in trace amounts within the Ampligen® mixture. A method is disclosed to enrich the Rugged dsRNA species so it becomes the dominant structure. Its rugged structure as measured by physico-chemical techniques is resistant to molecular unfolding (i.e., denaturation). Improvement in at least one or more biological activities may result from the rugged structure of this particular form of dsRNA. Other advantages and improvements are described below, or would be apparent from the disclosure herein.

The Eli Lilly and Company, U.S. Pat. No. RE 39,071E is an example of a newly discovered biochemical/biological intermediate in existing unimproved biochemical/biological mixtures of drugs resulting in patentability. (See also U.S. Pat. No. 6,468,967 and U.S. Pat. No. 6,852,689.)

SUMMARY OF THE INVENTION

It is an objective of the invention to provide new and improved forms of double-stranded ribonucleic acid (dsRNA). Their physico-chemical structure and biological activities are described herein. A "rugged" dsRNA molecule resistant to unfolding (i.e., denaturation) of its helical structure and a reduced tendency to form branched dsRNA molecular structures and having an improved dsRNA activity as a selective agonist of Toll-like receptor 3 (TLR3). At least partial purification of Rugged dsRNA from other dsRNA present after synthesis is expected to increase specificity in its use as a medicament and thereby reduce adverse effects attributable to the dsRNA that is not rugged.

Specifically-configured Ampligen® dsRNA mixture may be of the general formula ribo($I_n$)·ribo($C_{11-14}U$)$_n$, or ribo($I_n$)·ribo($C_{12}U$)$_n$, wherein the strands are comprised of ribonucleotides (ribo) and n is an integer from about 500 to about 2,000 repeats. For example, a strand comprised of poly(ribo-cytosinic$_{11-14}$uracilic acid), or poly(ribocytosinic$_{12}$uracilic acid) may be partially hybridized to an opposite strand comprised of poly(riboinosinic acid) such that the two strands form an RNA double helix that is not paired at the uracil base (i.e., mismatch).

After synthesis, Rugged dsRNA may be isolated from the Ampligen® mixture by at least subjecting the partially hybridized strands of a population of dsRNA to conditions that denature most dsRNA (at least 50 mol %, at least 80 mol %, at least 90 mol %, or at least 95 mol %) in the population, and then selection negatively or positively (or both) for dsRNA that remain partially hybridized. The purity of Rugged dsRNA may thus be increased from less than about 1-12 mol % (e.g., less than about 12 mol %) relative to all RNA in the population after synthesis. It is preferred that the Rugged dsRNA be more than about 80-98 mol % relative to all RNA present in the same mixture with the Rugged dsRNA (at least 80 mol %, at least 90 mol %, at least 95 mol %, or at least 98 mol %) after selection. The denaturing conditions to unfold at least partially hybridized strands of dsRNA may comprise appropriate choice of buffer salts, pH, solvent, temperature, or any combination thereof. Conditions may be empirically determined by observation of the unfolding or melting of the duplex strands of ribonucleic acid. The yield of Rugged dsRNA may be improved by partial hydrolysis of longer strands of ribonucleic acid, then selection of (partially) hybridized stands of appropriate size and resistance to denaturation.

The molecular weight of Rugged dsRNA may be from about 30 Kda to about 300 Kda, or from about 75 Kda to about 225 Kda. Lengths of a single or both strands of Rugged dsRNA may be from about 50 bases to about 500 bases, or from about 125 bases to about 375 bases. The number of helical turns made by duplexed RNA strands of Rugged dsRNA may be from about 4.7 to about 46.7, or from about 11.7 to about 35 helical turns.

In another aspect, at least one or more different Rugged dsRNA may be administered to a subject (e.g., human patient or animal) in need of such treatment. Rugged dsRNA may be administered at a dosage of from about 0.5 μg to about 600 mg/dose. This dosage may be administered once per week or month, or two or more doses per week or month. Each dose (e.g., from about 0.5 μg to about 600 mg, from about 1 mg to about 100 mg, or from about 10 mg to about 40 mg) may be provided to the subject without limitation to the formulation of the pharmaceutical composition, or its route of administration (although intravenous infusion is preferred). Use of an effective amount of Rugged dsRNA to achieve a feeling of improved health and may be continued until at least one symptom is improved. The effective amount required to obtain such improvement may be identical to or higher than the amount required for maintenance of the effect(s).

The Rugged dsRNA may act specifically through a TLR3 receptor. The function and phenotype of dendritic cells may be normalized in a subject (e.g., human patient or animal). Administering at least an effective amount of one or more Rugged dsRNA to a subject (e.g., human patient or animal) may thereby decrease the number or reduce the severity of symptoms when the subject is afflicted by a disease or other pathological condition. Use of Rugged dsRNA may correct dendritic cell maturation abnormalities in the subject without the hazard of inducing a cytokine storm.

Antigen presenting cells (e.g., dendritic cells, macrophages, B cells) and mucosal tissues (e.g., gastric or respiratory epithelium) are preferred targets in the body for Rugged dsRNA. One or more antigens may be presented to cells of the immune system, and the antigen(s) should be susceptible to the action of the Rugged dsRNA acting selectively as a TLR3 agonist. Cells of the immune system, microbes, cancer cells, or other transformed cells may be susceptible to specific cytokine response patterns activated by Rugged dsRNA acting selectively as a TLR3 agonist. The Rugged dsRNA is preferably administered by intravenous infusion; intradermal, subcutaneous, or intramuscular injection; intranasal or intratracheal inhalation; or oropharyngeal or sublingual application; or transocularly.

In another aspect, a medicament is provided as a pharmaceutical composition. One or more different Rugged dsRNA may be used for their beneficial effect(s) on a subject's health, as selective TLR3 agonist(s), to treat a disease or other pathological condition, or to manufacture medicaments or pharmaceutical compositions to treat a disease or other pathological condition. Optional inert ingredients of the composition include excipients and a vehicle (e.g., saline buffer or water) as a single dose or a multi-dose package (e.g., an injection vial or vials), and instructions for their use. Processes for making and using the pharmaceutical composition (medicament) are also provided. For example, one or more different Rugged dsRNA may be formulated at a concentration from about 0.05 mg/mL to about 0.25 mg/mL (e.g., 10 mg dissolved in 4 mL or 20 mg dissolved in 8 mL) in physiological phosphate-buffered saline and stored at from 2° C. to 8° C. in a refrigerator under aseptic conditions.

Further aspects of the invention will be apparent from our description of specific embodiments and the appended claims, and generalizations thereto.

BRIEF DESCRIPTION OF THE DRAWINGS

FIG. 2 shows. FDA analyses of the three HPLC peaks. Acetonitrile, which is used as a solvent, is responsible for the strong absorbance at 230 nm. Absorbance at 245 nm indicates the presence of poly(I); absorbance at 265 nm indicates the presence of poly($C_{12}U$).

FIG. 10 shows a CD plot of a thermal melt of single stranded poly ($C_{12}U$). A strong signal is apparent due to the chirality of cytidine. However, the absence of a second peak at 245 nm shows that intra molecular base stacking of Poly C12U does not occur.

FIG. 27 shows two typical examples of the branched dsRNA structure contained in the unimproved Ampligen® mixture.

FIG. 29 shows typical examples of unbranched dsRNA molecules contained in the new/improved Rugged dsRNA.

DESCRIPTION OF SPECIFIC EMBODIMENTS

Definitions dsRNA

Double-stranded (ds) RNA (ribonucleic acid) is chemically very similar to DNA (deoxyribonucleic acid). It is also a long molecule containing nucleotides linked together by 3'-5' phoshodiester bonds. Two differences in its chemical groups distinguish dsRNA from DNA. The first is a minor modification of sugar component. The sugar of DNA is deoxyribose, where as RNA contains ribose, which is identical to deoxyribose except for the presences of an additional hydroxyl group. The second difference is that RNA contains no thymine, but instead contains the closely related pyrimidine, uracil. DsRNA forms from the hyridization of two complementary polyribonucleotides forming a double helix similar to that of DNA. The two strands of the double helix are held together by hydrogen-bonded base pairs.

Ampligen®

Ampligen® is a particular dsRNA denoted Poly I: Poly $C_{12}U$, wherein one of the two polyribonucleotides is polyriboinosinic acid and the other is polyribocytidylic$_{12}$, uridylic acid. Thus, the pyrimidine building blocks of Ampligen® are present in a ratio of 12 cytosines of each uracil, while the complementary purine strand contains 13 inosine residues. Within the double-stranded helical structure of Ampligen® the pyrimidine, cytosine, hydrogen bonds with the purine, inosine, while the pyrimidine, uracil, does not form any hydrogen bonds. Therefore, a "mismatch" is created once for every 12 base pairs (bps) formed between the inosine and cytosine residues. In contrast to Ampligen®, Poly I: Poly C contains only complementary inosine: cytosine base pairs. No uracil is present in Poly I: Poly C and there are no mismatches.

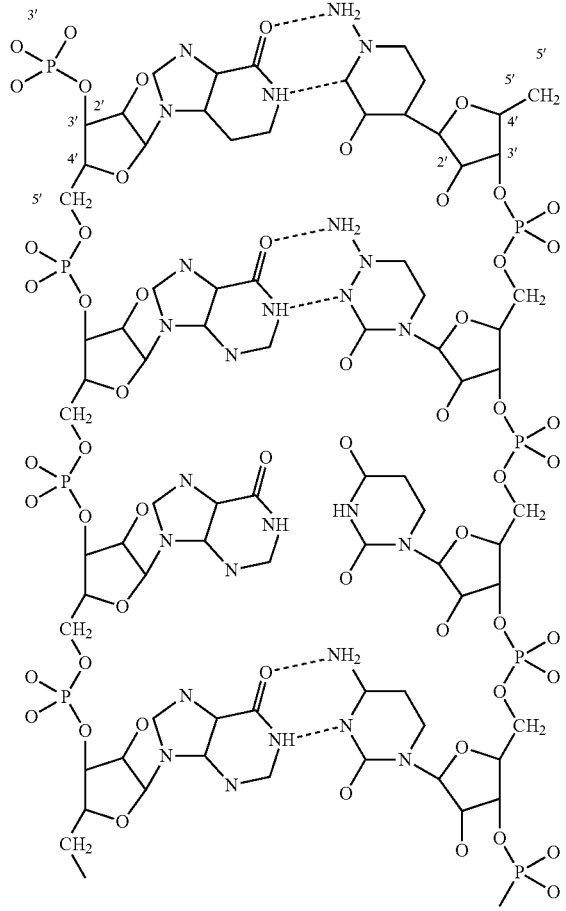

TLR3 (Toll-Like Receptor 3)

Figure 24:
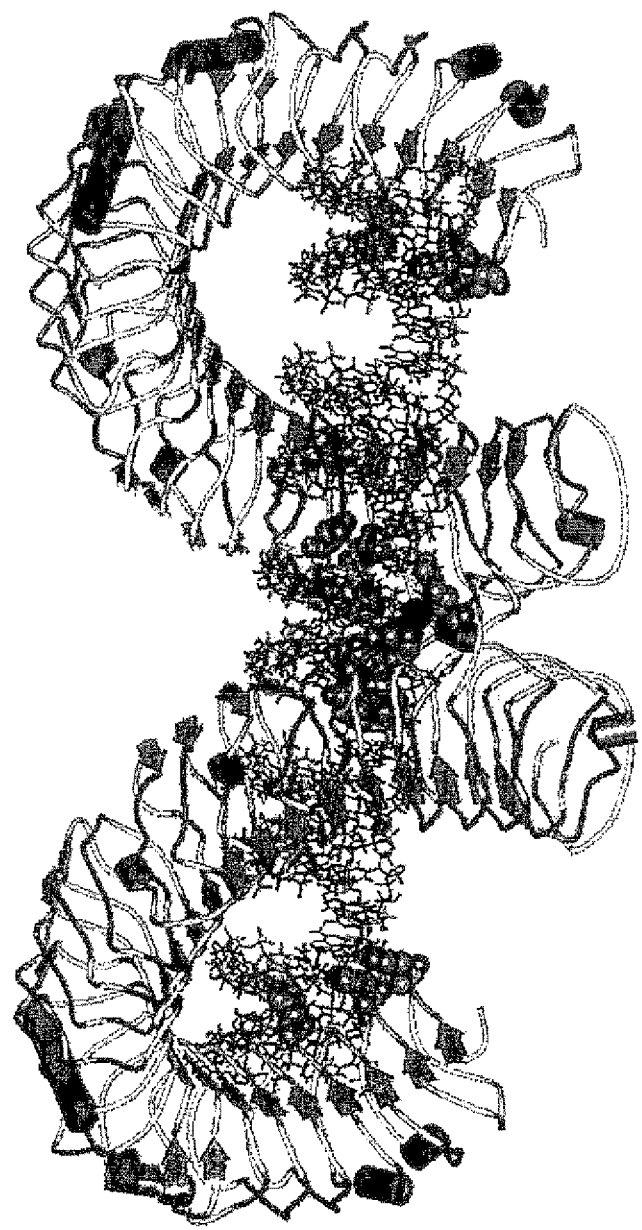
FIG. 24. is a lateral view of Rugged dsRNA (a minor component in the unimproved Ampligen® mixture) bound to the active site of the TLR3 homodimer (2 horseshoe shaped structures). The C-terminal regions of each dimer face each other and bind to the phosphate backbone of the dsRNA. The N-terminals of each TLR3 bind to opposite ends of the dsRNA with a minimum length of 50 bp required for interaction with essential residues of TLR3 for activation of intracellular signaling. Amino acids of TLR3 required for binding of Rugged dsRNA are shown using Van der Waals' radii associated with the phosphate backbone.
Figure 25:
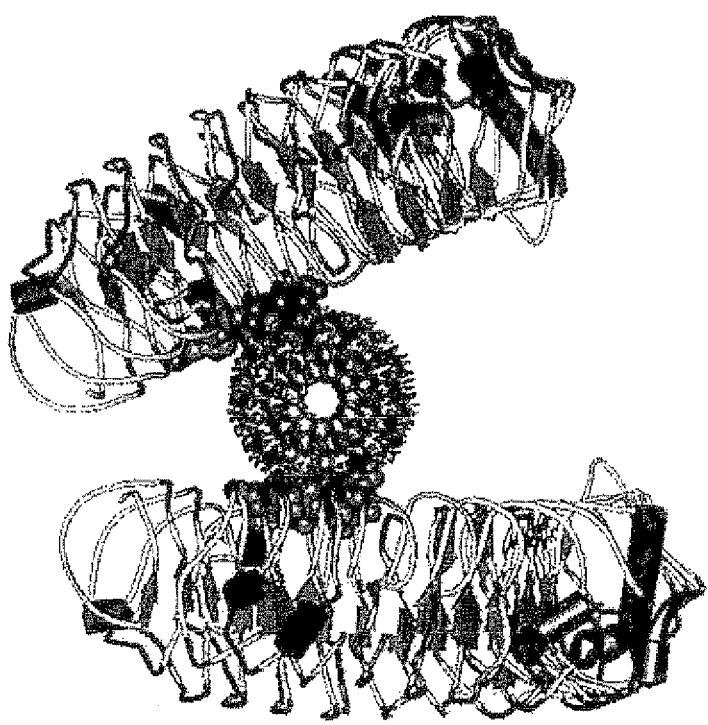
FIG. 25. Illustrates the TLR3 homodimer complexed with Rugged dsRNA (a minor component in the unimproved Ampligen® mixture) as seen down the long axis of the dsRNA.

TLR3 is a receptor for a form of immunity called "innate immunity" which recognizes double-stranded RNAs with a minimum size of at least 50 base pairs. The size requirement or discrimination of dsRNA by TLR3 prevents responses to non-microbial sources of dsRNA micro (mi) RNA or transfer (t) RNA. TLR3 exists as a horseshoe shaped monomer with a N-terminal, ligand-binding extra-cytoplasmic domain (ECD), a transmembrane domain (TMD), and a C-terminal cytoplasmic signaling domain (CSD). X-ray crystallographic studies have provided structural data for the TLR-3 ligand complex which consists of a TLR3 homo-dimer complexed to dsRNA of at least about 50 consecutive base pairs. The formation of the complex (FIG. 24) is believed to transmit a conformational change in the CSD via the TMD connector that allows cytoplamic signaling. Above 50 base pairs, binding affinity is a function of size with a progressive increase in binding affinity with increased length in linear non-branched dsRNA.

Rugged dsRNA

Figure 21:
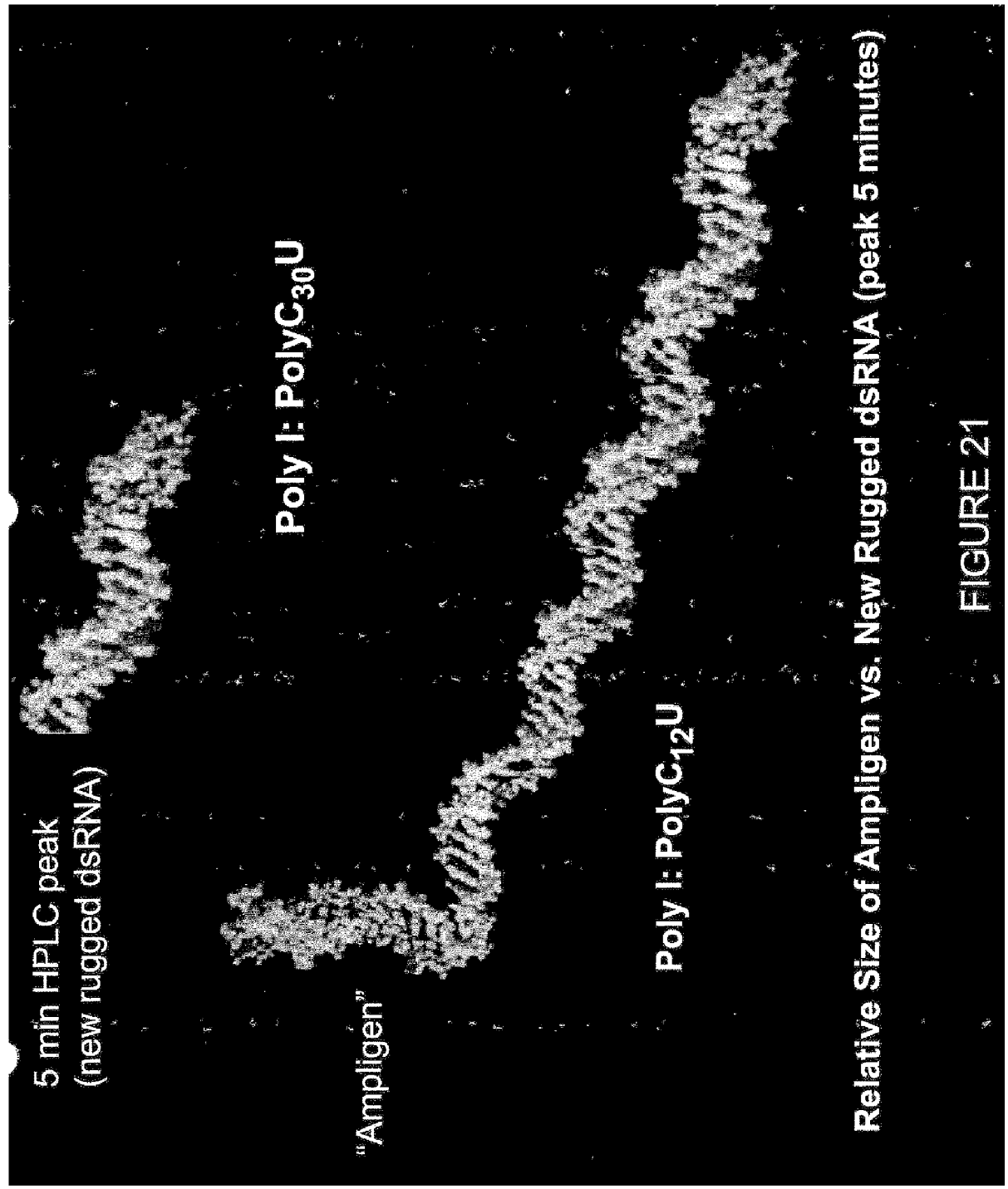
FIG. 21 shows the relative size of Ampligen® vs new Rugged dsRNA (peak 5 minutes).

Rugged dsRNA is a novel form of dsRNA with a unique composition and physical characteristics. Unlike the previously known antiviral, Ampligen® (Poly I: Poly $C_{12}U$), the new and improved form of Rugged dsRNA (e.g., Poly I: Poly $C_{30-35}U$ (preferably, Poly I: Poly $C_{30}U$), wherein PolyC$_{30-35}$U, indicates a ratio, that is, that for every U there are 30-35 C's), has an increased Ruggedness characterized by an increase resistance to thermal denaturation and ribonuclease digestion. This improved form of dsRNA also has a reduced tendency to form branched dsRNA molecules which results in a increased bioactivity due to an increased ability to bind TLR3 receptor. The minimal length of Rugged dsRNA (termed the monomer unit) is about 50 base pairs requiring about 4 to 5 (e.g., 4.7) helical turns (10.7 base pairs are required for each complete turn of the helix) within its dsRNA structure and represents the smallest or monomeric unit of Poly I: Poly $C_{30}U$, approximately 24,000 to 30,000 Daltons (a Dalton is a unit of weight equal to the weight of a single hydrogen atom). The maximal length of Rugged dsRNA is about 500 base pairs composed of about 10 monomer units, requiring about 50 (e.g., 46.7) helical turns and having a molecular weight of approximately 300,000 Daltons (e.g., about 225,000 Daltons). FIG. 21 shows the relative size of the old unimproved Ampligen® vs. the New improved Rugged dsRNA.

Branched dsRNA

Figure 26:
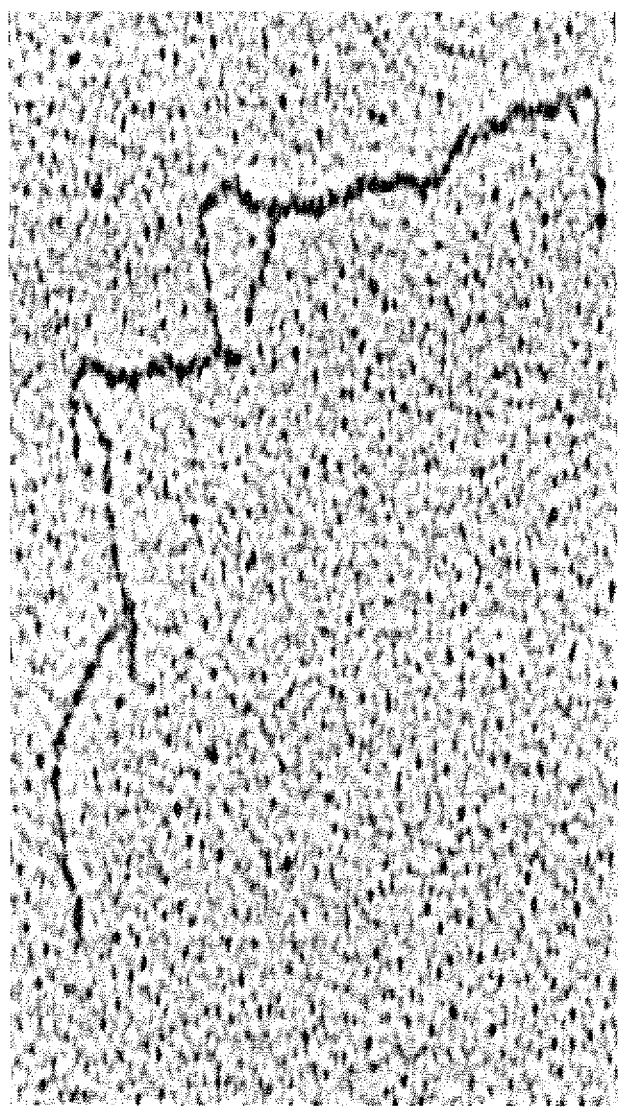
FIG. 26. Shows a typical example of a branched dsRNA structure contained in the unimproved Ampligen® mixture.
Figure 28:
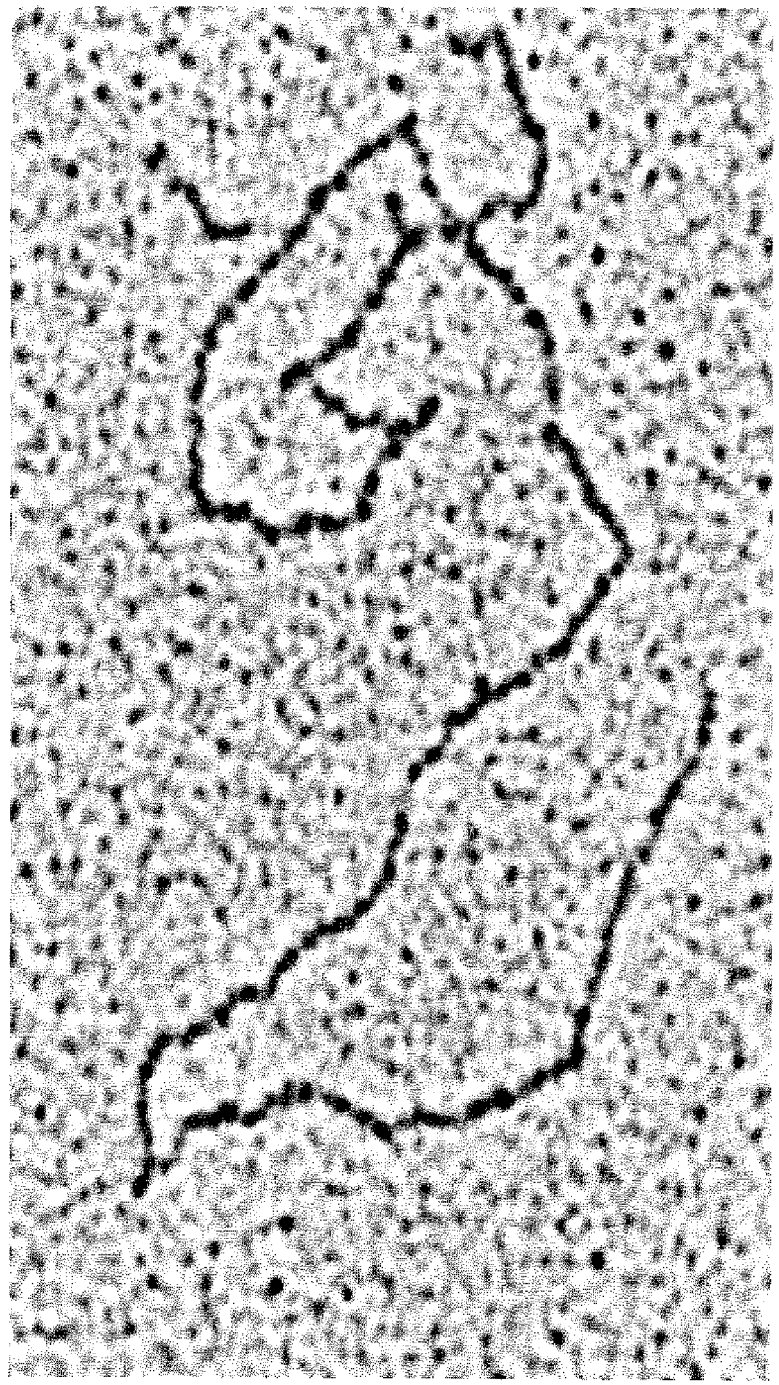
FIG. 28 shows a typical example of a more complexed branched dsRNA structure contained in the unimproved Ampligen® mixture.

Branching is seen as the major configuration of dsRNA molecules within the Ampligen® unimproved mixture. FIGS. 26, 27, and 28 show typical examples of the branching molecules seen by Transmission Electron Microscopy (TEM) in the unimproved Ampligen® mixture of dsRNA molecules. The branching in the molecules interferes with TLR3 binding. Ampligen® has 4-5 times more molecules with ≥3 branched strands than Rugged dsRNA and, therefore, Ampligen® has reduced bioactivity relative to the new and improved Rugged dsRNA (e.g., Poly I: Poly $C_{30-35}U$ (preferably, Poly I: Poly $C_{30}U$)). This explains the increased bioactivity of Rugged dsRNA compared to the unimproved Ampligen® mixture. Typical examples of the major component of Rugged dsRNA (unbranched dsRNA molecules) are shown in FIG. 29.

RNA Helix

A spiral structure of dsRNA with a repeating pattern described by two simultaneous operations (rotation around the axis and translation along the axis). DsRNA requires the translation of 10.7 base pairs to complete one complete rotation around the axis (i.e. one helical turn).

Dalton

A unit of weight equal to the weight of a single hydrogen atom. One Kda=1000 Daltons Rugged dsRNA Monomer The minimum active size of Rugged dsRNA comprised of about 40-50 base pairs, requiring about 4-5 (e.g., 4.7) helical turns and having a molecular weight of approximately 24,000 to 30,000 Daltons.

Rugged dsRNA Polymeric Units

Rugged dsRNA composed of multiple monomeric units (or fractional units thereof) of Rugged dsRNA up to a maximum of about 10 monomeric units held together by covalent phosphodiester bonds in a linear structure. The maximum Rugged dsRNA molecular size contains about 500 base pairs, requiring about 50 (e.g., 46.7) helical turns and having a molecular weight of approximately 300,000 Daltons (e.g., about 225,000 Daltons).

Many uses of double-stranded ribonucleic acid (dsRNA) are known. Efficacy of such treatments, which includes a decrease in the number and/or a reduction in the severity of adverse effects of nonselected populations of dsRNA, is improved by the use of at least partially purified, Rugged dsRNA. The invention may be used to treat a subject (e.g., human or animal, especially birds, fishes, or mammals) with an incipient or established microbial infection, to treat a subject for other pathological conditions marked by abnormal cell proliferation (e.g., neoplasm or tumor), or for use as an immunostimulant to treat the subject for a disease or other pathological condition caused by at least infection, abnormal cell proliferation, chronic fatigue syndrome, or cell damage from autoimmunity or neurodegeneration. It is preferred that the amount of Rugged dsRNA used is sufficient to bind Toll-Like Receptor 3 (TLR3) on immune cells of the subject. Innate or adaptive immunity may be triggered thereby. Preferably, Rugged dsRNA may be used to activate TLR3 selectively without activating other Toll-like receptors like TLR4 or an RNA helicase like RIG-I or mda-5, or without inducing an excessive pro-inflammatory response as seen with the nonselective TLR3 agonist poly (I):poly(C) in a phenomenon known as "cytokine storm" in the art.

The subject may be infected with at least one or more bacteria, protozoa, or viruses. A pharmaceutical composition which is comprised of Rugged dsRNA in an amount sufficient to bind to TLR3 is administered to the subject. Infection of the subject is reduced or eliminated thereby as assayed by decreased recovery time, increased immunity (e.g., increase in antibody titer, lymphocyte proliferation, killing of infected cells, or natural killer cell activity), decreased division or growth of the microbe, or any combination thereof as compared to the subject not treated with the Rugged dsRNA. The immunity induced by treatment is preferably specific for the microbe, although inducing innate immunity may also be efficacious.

An infection by a microbe may be treated. The microbe may infect a human or animal subject. The infection may be incipient or established. The microbe may be a bacterium, protozoan, or virus; especially those that cause disease (i.e., pathogenic microbes). Here, the terms "microbe" and "micro-organism" are used interchangeably.

The bacterium may be a species of the genus *Bacillus* (e.g., *B. anthracis, B. cereus*), *Bartonella* (*B. henselae*), *Bordetella* (e.g., *B. pertussis*), *Borrelia* (e.g., *B. burgdorferi*), *Brucella* (e.g., *B. abortus*), *Campylobacter* (e.g., *C. jejuni*), *Chlamydia* (e.g., *C. pneumoniae*), *Clostridium* (e.g., *C. botulinum, C. difficile, C. perfringens, C. tetani*), *Corynbacterium* (e.g., *C. amycolatum, C. diphtheriae*), *Escherichia* (e.g., *E. coli* O175:H7), *Haemophilus* (e.g., *H. influenzae*), *Heliobacter* (e.g., *H. pylori*), *Klebsiella* (*K. pneumoniae*), *Legionella* (e.g., *L. pneumophila*), *Listeria* (e.g., *L. monocytogenes*), *Mycobacterium* (e.g., *M. avium, M. bovis, M. branderi, M. leprae, M. tuberculosis*), *Mycoplasma* (e.g., *M. genitalium, M. pneumoniae*), *Neisseria* (e.g., *N. gonorrheae, N. meningitidis*), *Pneumocystis* (e.g., *P. carinii*), *Pseudomonas* (*P. aeruginosa*), *Rickettsia*, (e.g., *R. rickettsia, R. typhi*), *Salmonella* (e.g., *S. enterica*), *Shigella* (e.g., *S. dysenteriae*), *Staphylococcus* (e.g., *S. aureus, S. epidermidis*), *Streptococcus* (e.g., *S. pneumoniae, S. pyogenes*), *Treponema* (e.g., *T. pallidum*), *Vibrio* (e.g., *V. cholerae, V. vulnificus*), or *Yersinia* (e.g., *Y. pestis*). These include Gram-negative or Gram-positive bacteria, chlamydia, spirochetes, mycobacteria, and mycoplasmas.

The protozoan may be a species of the genus *Cryptosporidium* (e.g., *C. hominis, C. parvum*), *Entamoeba* (e.g., *E. histolytica*), *Giardia* (e.g., *G. intestinalis, G. lamblia*), *Leishmania* (e.g., *L. amazonensis, L. braziliensi, L. donovani, L. mexicana, L. tropica*), *Plasmodium* (e.g., *P. falciparum, P. vivax*), *Toxoplasma* (e.g., *T. gondii*), or *Trypanosoma* (e.g., *T. bruci, T. cruzi*).

The virus may be a DNA or RNA virus that infects humans and animals. DNA viruses include those belonging to the Adenoviridae, Iridoviridae, Papillomaviridae, Polyomaviridae, and Poxviridae families (Group I double-stranded DNA viruses); the Parvoviridae family (Group II single-stranded DNA viruses). RNA viruses include those belonging to the Birnaviridae and Reoviridae families (Group III double-stranded RNA viruses); the Arteriviridae, Astroviridae, Caliciviridae, Hepeviridae, and Roniviridae families (Group IV positive single-stranded RNA viruses); and the Arenaviridae, Bornaviridae, Bunyaviridae, Filoviridae, Paramyxoviridae, and Rhabdoviridae families (Group V negative single-stranded RNA viruses). Rugged dsRNA may also be used to treat infection by DNA viruses from the Herpesviridae family and RNA viruses from the Flaviviridae, Hepadnaviridae, Orthomyxoviridae, Picornaviridae, Retroviridae, and Togaviridae families.

The subject may be afflicted by a disease or pathological condition that is characterized by abnormal cell proliferation (e.g., neoplasm or tumor, other transformed cells). A pharmaceutical composition which is comprised of Rugged dsRNA in an amount sufficient to bind to TLR3 is administered to the subject. Disease, symptoms thereof, their number, or their severity in the subject may be reduced or eliminated thereby as assayed by improved morbidity or mortality, increased immunity (e.g., increase in antibody titer, lymphocyte proliferation, killing proliferating or transformed cells, or NK cell activity), decreased division or growth of proliferating or transformed cells, or any combination thereof as compared to the condition of a subject not treated with Rugged dsRNA.

The subject's cells undergoing the abnormal proliferation may be a neoplasm or tumor (e.g., carcinoma, sarcoma, leukemia, lymphoma, glioma), especially cells transformed by a tumor virus (e.g., DNA or RNA virus carrying a trans-forming gene or oncogene) or otherwise infected by a virus associated with cancer. For example, Epstein-Barr virus is associated with nasopharyngeal cancer, Hodgkin's lymphoma, Burkitt's lymphoma, and other B lymphomas; human hepatitis B and C viruses (HBV and HCV) are associated with liver cancer; human herpesvirus 8 (HHV8) is associated with Kaposi's sarcoma; human papillomaviruses (e.g., HPV6, HPV11, HPV16, HPV18, or combination thereof) are associated with cervical cancer, anal cancer, and genital warts; and human T-lymphotrophic virus (HTLV) is associated with T-cell leukemia and lymphoma. Cancers include those originating from the gastrointestinal (e.g., esophagus, colon, intestine, ileum, rectum, anus, liver, pancreas, stomach), genitourinary (e.g., bladder, kidney, prostate), musculoskeletal, nervous, pulmonary (e.g., lung), or reproductive (e.g., cervix, ovary, testicle) organ systems.

Dendritic cell maturation may be induced in the subject. Immature dendritic cells, which are capable of antigen uptake, may be induced to differentiate into more mature dendritic cells, which are capable of antigen presentation and priming an adaptive immune response (e.g., antigen-specific T cells). During their conversion from immature to mature dendritic cells, they may at least change cell-surface expression of major histocompatibility complex (MHC) molecules, costimulatory molecules, adhesion molecules, or chemokine receptors; decrease antigen uptake; increase secretion of chemokines, cytokines, or proteases; grow dendritic processes; reorganize their cytoskeleton; or any combination thereof. They may be induced to migrate to sites of inflammation or lymphoid tissue through blood or lymph to bring microbes, neoplastic or tumor cells, or other transformed cells into proximity.

The subject may be vaccinated against at least infection (e.g., microbial infection) or cancer. The vaccine can be, for example, an anti-viral anti-protozoan or anti-bacterial vaccine. In some cases, e.g., virus-induced cancers, both infection and cancer may be treated. Immediately before, during, or 11D immediately after vaccination (e.g., within 10 days of vaccination), a medicament or pharmaceutical composition which is comprised of Rugged dsRNA in an amount sufficient to bind to TLR3 is administered to the subject. The immune response to a vaccine or dendritic cell preparation is stimulated thereby. The vaccine or dendritic cell preparation may be comprised of killed, fixed, or attenuated whole microbes or cells (e.g., proli-ferating or transformed); a lysate or purified fraction of microbes or cells (e.g., proliferating or transformed); one or more isolated microbial antigens (e.g., native, chemically synthesized, or recombinantly produced); or one or more isolated tumor antigens (e.g., native, chemically synthesized, or recombinantly produced). in situ vaccination may be accomplished by the subject's production of antigen at a site or circulation thereto (e.g., produced in a natural infection or cell growth, or shed antigen), and Rugged dsRNA acting as an adjuvant thereon. The dsRNA can be administered sequentially or concurrently with the vaccine.

Rugged dsRNARugged dsRNA

Rugged dsRNA as at least a portion of a medicament or formulated with other compatible components in a pharmaceutical composition may be administered to a subject (e.g., human patient or animal, especially birds, fishes, or mammals) by any local or systemic route known in the art including enteral (e.g., oral, feeding tube, enema), topical (e.g., device such as a nebulizer for inhalation through the respiratory system, skin patch acting epicutaneously or transdermally, suppository acting in the rectum or vagina), and parenteral (e.g., subcutaneous, intravenous, intramuscular, intradermal, or intraperitoneal injection; buccal, sublingual, or transmucosal; inhalation or instillation intranasally or intratracheally). The Rugged dsRNA may be micronized by milling or grinding solid material, dissolved in a vehicle (e.g., sterile buffered saline or water) for injection or instillation (e.g., spray), topically applied, or encapsulated in a liposome or other carrier for targeted delivery. Dissolving the Rugged dsRNA in water for injection (WFI) and injection of the composition into the subject are preferred. A carrier may be used to target the Rugged dsRNA to the TLR3 receptor on antigen presenting cells and epithelium. For example, immature dendritic cells may be contacted in skin, mucosa, or lymphoid tissues. It will be appreciated that the preferred route may vary with the age, condition, gender, or health status of the subject; the nature of disease or other pathological condition, including the number and severity of symptoms; and the chosen active ingredient.

Formulations for administration (i.e., pharmaceutical compositions) may include aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. It will be appreciated that the preferred formulation may vary with the age, condition, gender, or health status of the subject; the nature of disease or other pathological condition, including the number and severity of symptoms; and the chosen active ingredient.

The recommended dosage of Rugged dsRNA will depend on the clinical status of the subject and the physician's or veterinarian's experience treating the disease or other pathological condition. Rugged dsRNA may be dosed at from about 0.5 µg to about 600 mg, from about 1 mg to about 100 mg, or from about 10 mg to about 40 mg in a subject (e.g., body mass of about 70-80 Kg for a human patient) on a schedule of once to thrice weekly (preferably twice weekly), albeit the dose amount and/or frequency may be varied by the physician or veterinarian in response to the subject's symptoms. Nucleic acid in solid form may be dissolved in physiological phosphate-buffered saline and then infused intravenously. Cells or tissues that express TLR3 are preferred sites in the subject for delivering the nucleic acid, especially antigen presenting cells (e.g., dendritic cells, macrophages, B lymphocytes) and endothelium (e.g., endothelial cells of the respiratory and gastric systems). It will be appreciated that the preferred dosage may vary with the age, condition, gender, or health status of the subject; the nature of disease or other pathological condition, including the number and severity of symptoms; and the chosen active ingredient.

Dendritic cells which act as sentinel cells possess molecular surface structures that recognize pathogen-associated molecular patterns (PAMPs). These PAMPs include a set of Toll-like receptors (TLRs) that specifically recognize all dsRNA. In particular, dsRNA is a selective agonist of TLR3. Rugged dsRNA may be used as a selective agent for activation of TLR3. Dysfunction in co-stimulatory molecule (e.g., CD80, CD83, CD86) signaling in dendritic cells may be associated with the disease or other pathological condition to be treated. This abnormality may be normalized by using Rugged dsRNA as a selective TLR3 agonist. The effects of Rugged dsRNA may be inhibited or blocked by mutation of the TLR3 gene (e.g., deletion), down regulating its expression (e.g., siRNA), binding with a competitor for TLR3's ligand-binding site (e.g., neutralizing antibody) or a receptor antagonist, or interfering with a downstream component of the TLR3 signaling pathway (e.g., MyD88 or TRIF).

Circular dichroism (CD) is a physico-chemical technique for characterizing the conformation of specifically-configured dsRNA. It can also be used as a surrogate for binding of Ampligen®dsRNA as a receptor agonist to its receptor TLR3, Furthermore, the helical structure of Rugged dsRNA and the structural requirements for binding of dsRNA to TLR3 can be precisely characterized by CD.

Other physico-chemical techniques that may be used to characterize Rugged dsRNA are reverse phase chromatography, PDA (photodiode array) analysis, gas pressure chromatography (GPC), specific ligand binding to TLR3 receptor, and sedimentation velocity measured by ultracentrifugation.

Rugged dsRNA provides a selective agent for dissecting out the effects of TLR3 activation on the immune system that was not previously available with such potency. Other agents like TLR adapters MyD88 and TRIF mediate signaling by all TLR or TLR3/TLR4, respectively. Thus, activation or inhibition of signaling through MyD88 or TRIF would not restrict the biological effects to those mediated by TLR3. Since the presence of TLR3 and its signaling is a requirement for Ampligen® poly(I):poly($C_{12}U$) to act as a receptor agonist, one could assay for the absence of TLR3 mutations, the presence of TLR3 protein, intact TLR3-mediated signaling, or any combination thereof in the cell or tissue of a subject prior to administration of the agonist. Such confirmation of TLR3 activity can be performed before, during, or after administration of the agonist. The agonist can be used to restrict the immune response to activation of TLR3 without activating other Toll-like receptors or RNA helicases. For example, abnormal cytokine (e.g., IFN-α, IFN-β, IFN-γ, TNF-α, IL-6, IL-10, IL-12) production or co-stimulatory molecule (e.g., CD80, CD83, CD86) signaling may have resulted from at least infection by the microbe, abnormal cell proliferation, autoimmune damage, or neurodegeneration. This abnormality may be remodulated by using Rugged dsRNA as a selective agonist of TLR3. Antigen presentation may be improved by conjugating the antigen (or a peptide analog thereof) to a ligand (or a receptor) that specifically binds to the cell surface (especially a component of the endosome-phagosome internalizing pathway) of one or more antigen presenting cells. The specific binding molecule may be an antibody to a cell surface molecule, or a derivative thereof (e.g., Fab, scFv).

Expression of CD80, CD83, and CD86 may be analyzed by flow cytometry using fluorescently-labeled antibodies. Following overnight shipment, blood samples are stained within one hour of receipt. Conventional techniques are used for lysis of red blood cells and cell marker analyses by flow cytometry. Dendritic cells are identified based on low level expression of lymphocyte, monocyte, and NK cell markers along with high HLA-DR expression. Dendritic cells may also characterized according to CD11c and CD123 expression. Monocytes are identified by side scatter analysis and expression of a monocyte lineage marker. Analyses of CD80, CD83, and CD86 expression are performed after cell type identification. Measurements from healthy volunteers serve as controls, and they would indicate normal distribution and levels of marker expression for mature dendritic cells such as CD80, CD83, and CD86.

Rugged dsRNA can be prepared by chromatographic separation, wherein Rugged dsRNA is separated from the majority of unimproved dsRNA.

An exemplary chromatographic procedure involves the following steps:

1. Binding of all forms of unimproved dsRNA to a reversed phase chromatography resin. The resin contains hydrophobic functional groups. In the current example the resin is Phenomenex, Polymerx, RP-1, but may alternately be selected from a range of commercially available hydrophobic resins as directed by conventional practice. Resin particle size is 10 microns in the current example, but may be varied widely to afford optimal separations or to produce Rugged dsRNA at differing scales of operation.

2. The dsRNA is injected as a solution of 2.5 mg/ml in phosphate buffered saline, pH 7.0, in the current example. The concentration and pH range can be varied to include alternative appropriate buffering systems utilized by those familiar with the art. The diluent can also contain stabilizing elements such as magnesium. The ionic strength, 200 mM in the current example, can be varied to achieve optimal loading and separation performance conditions as directed by conventional practices.

3. The mobile phase composition contains a relatively polar organic solvent to modulate binding during loading and the subsequent, gradient elution. In the current example, the mobile phase contains acetonitrile at an initial loading concentration of 6-8 vol % which produces enriched Rugged dsRNA fractions during the gradient elution to 20 volume %. Alternative solvent systems can be selected having optimal solvent concentration ranges as directed by conventional practice.

4. The sample loading is 13 mg unimproved dsRNA/ml column. Loading can be decreased to afford tighter fractionation of Rugged dsRNA. Alternative combinations of solvent and ionic strength will require individually determined optimal loading conditions as directed by conventional practice.

5. The mobile phase flow rate for sample loading and elution range is 5 ml/min in the current example (3 column volumes/hr). The flow rate can be varied to achieve optimal conditions for differing scales of operation and resin particle size as directed by conventional practice.

6. Elution is achieved by imposing a solvent gradient to the composition of the mobile phase. In the current example, the gradient of acetonitrile composition is increased from the loading condition of 6-8% to 20%, over a period of 14 minutes. The type of solvent and the gradient profile can be altered based upon the character of the hydrophobic functionality as determined by conventional practices.

7. In the current example, improved Rugged dsRNA is collected at 10-12 minutes or 0.25-0.30 column volumes. The peak location can vary depending upon alternative choices of solvent, flow rate, column type as provided above.

One skilled in the art will appreciate that separations suitable for isolation of Rugged dsRNA can be scaled up for commercial purposes.

EXAMPLES

Synthesis of single-stranded poly(I) and poly($C_{12}U$) began with enzymatic polynucleotide synthesis of the polynucleotides from the respective mononucleotide starting materials: inosine for poly(I); cytidine (C) and uridine (U) for poly($C_{12}U$). Then repetitive extraction and precipitation steps were used to remove residual impurities. The reaction solutions containing the products were concentrated by ultrafiltration and extracted with phenol four times. The concentrated and extracted solutions were precipitated, dissolved, and re-precipitated from aqueous ethanol (50:50). Whereas precipitated poly(I) was separated by centrifugation, the supernatant (waste) liquid phase of adherent poly($C_{12}U$) was simply removed by aspiration. The precipitated pastes were re-dissolved, then concentrated, diafiltered, and further concentrated. The final bulk solutions containing polynucleotide was filtered. The filtered solution was freeze dried and the raw materials were stored frozen.

Enzymatic Synthesis.

The enzymatic synthesis used in the manufacturing process is dependent on the enzyme polynucleotide phosphorylase to synthesize polyinosinic acid and polycytidilic$_{12}$uridilic acid from their respective starting materials: cytidine 5'-diphosphate, trisodium salt (CDP.Na$_3$), uridine 5'-diphosphate, disodium salt (UDP.Na$_2$) and inosine 5'diphosphate, trisodium salt (IDP.Na$_3$).

The enzyme catalyzes polynucleotide formation in a reversible reaction using $Mg^{++}$ as a co-factor and ATP as a source of energy. Polynucleotides were synthesized in the 5' to 3' direction with concurrent liberation of inorganic phosphate. Maximum yield was limited by the equilibrium between synthesis and reverse rates, degradative reaction (phosphorolysis). The progress of the reaction was followed by measuring the consumption of CDP or IDP. Viscosity of the reaction solution was also monitored. Purified water was filtered into the tank. The following ingredients were added to the tank one at a time with mixing: TRIS (hydroxymethyl) aminomethane, urea, magnesium chloride hexahydrate (MgCl.6H$_2$0), and ethylenediaminetetraacetic acid (edetate), disodium salt (EDTA.Na$_2$). Raw material mononucleotides were also added.

Each ingredient was dissolved before the next one was added. After all of the ingredients were added, the solution was mixed for a minimum of 10 minutes. The mixture was then adjusted and purified water was added to obtain a final batch volume. This pre-enzyme reaction mixture was sampled for initial CDP or IDP concentration. The enzyme polynucleotide phosphorylase was added with mixing, whereupon the synthesis of polynucleotide commenced. Also, the viscosity profile at the optimal enzyme concentration must exhibit the usual increase in viscosity over time without significant decrease at the conclusion of the batch reaction; significant decrease in viscosity would indicate undesired degradation of polynucleotide. After the optimized amount of enzyme was added to the production batch, enzymatic synthesis progressed under constant, controlled agitation. The consumption of CDP or IDP was monitored approximately every hour. The reaction was terminated by the addition of a stop solution. Viscosity was also monitored, for information only, during the process.

Concentration of Reaction Solution.

To minimize the required volume of phenol for extractions, the reaction product solution was concentrated.

Extraction of dsRNA Mixture.

Residual enzyme was removed predominately by phenol extraction. The concentrated single stranded RNA reaction product solutions were transferred into separate extraction tanks and 2M TRIS and sodium dodecyl sulfate (SDS) were added. After at least 5 minutes of mixing, liquefied phenol was added and the two phase solution was mixed to disperse the phenol phase in the aqueous phase. SDS was employed as a surface-active agent to facilitate dissolution of denatured protein into the phenol phase; TRIS was required to buffer the solution at an optimal pH for polynucleotide stability. The extraction mixture stands without mixing for pre-determined settling times to afford coalescence of the phases. The lower phenol waste phase is then pumped into containers for disposal. The location of the phenol cut was important in order to effectively separate phenol and protein from the upper, product phase, which contains single stranded RNAs. The phenol phase and an intermediate "rag" layer, which contains denatured protein solids, were discarded by visually observing the liquid flowing through the site glass at the tank outlet. When the phenol and rag layer disappeared and only product phase was observed, the outlet valve was closed and the phenol cut is considered complete.

Precipitation of Single Stranded RNAs.

Contaminating phenol, SDS, and other salts remaining in solution were removed by precipitation with denatured ethyl alcohol. The single stranded RNA concentrated solution was pumped into the precipitation tank. The denatured alcohol was added and after mixing the precipitate was separated.

Concentration and Diafiltration.

Remaining bulk salts, a small amount of unreacted mononucleotide, and phenol were removed by diafiltration against water. The precipitate was dissolved in the original precipitation vessel with gentle mixing and heating. After dissolving, the solution was then concentrated and diafiltered against water for injection (WFI). The solution was filtered prior to freeze drying.

Freeze Drying.

The filtered single stranded RNA material was loaded into a freeze drier. The material was frozen, and a vacuum was then applied. The product was considered dry when the programmed cycle was complete.

Manufacture of dsRNA, Sterile Solution, for Intravenous Infusion.

The single stranded RNAs were dissolved in phosphate-buffered saline. Equal molar amounts were mixed in an annealing step, and cooled to room temperature. The solutions were sterile filtered.

Preparation of Buffer Vehicle, Excipient Solution.

WFI was added to the tank. The excipients were added to the tank, and mixed. After mixing, the batch was sampled for pH and osmolality. Quality control must be within in-process limits prior to use for formulating the solutions.

Formulating Poly(I) and Poly($C_{12}U$) Solutions.

An initial quantity of buffer solution was subdivided according to the batch formula and was filtered into the tank. The single stranded RNAs were added to the buffer solution, and dissolved by mixing. The temperature of the solution was increased and maintained with mixing. The solution is then recirculated.

Annealing of Poly I:Poly $C_{12}U$ Strands.

Equivalent quantities of poly(I) and poly($C_{12}U$) were transferred to the tank. With continual mixing, the temperature of the solution was increased. Samples were removed and tested for potency, and pH.

Sterile Filtration. The formulated bulk was sterile filtered in-line into a steam sterilized surge vessel.

Filling Operations.

The filling operation was performed. After each vial was filled, a sterile stopper is used to stopper the vial. Stoppered vials were then conveyed from the aseptic processing area where they were sealed.

Rugged dsRNA was isolated from the annealed poly(I):poly($C_{12}U$) mixture, which was prepared according to the above, by either analytical or preparative high performance liquid chromatography (HPLC) as a substantially purified and pharmaceutically-active molecule. Its molecular weight is from about 30 Kda to 300 Kda and is about 50 to 500 base pairs in length with about 4.7 to 46.7 complete turns of the RNA helix. It is only from about 4 mol % to about 16 mol % of an unfractionated Ampligen® composition. Most dsRNA (over 80 mol % molecules) after synthesis have a molecular weight of about 1.2 Mda and are about 2000 base pairs in length with about 187 complete turns of the RNA helix. The Rugged dsRNA in the 5 min HPLC peak is about 4 to 40 times smaller than the bulk of the dsRNA, and more closely fits the ligand binding site of its cell surface receptor (TLR3).

Due to its structure, Rugged dsRNA is unusually resistant to disruption of its RNA double helix and molecular unfolding. Thus, Rugged dsRNA under the assay conditions described herein has about 100- to about 1,000% greater bioactivity than the same weight of unimproved Ampligen® poly(I):poly($C_{12}U$).

(a) Protection by mismatched dsRNA is by Selective Activation of TLR3

TLR3 Activation is Linked to Expression of IFN-α/β, IL-6, or IL-12. The relationship between IFN expression through TLR3 activation by dsRNA was established by Alexopoulou (2001) using 293T cells that express different Toll-like receptors (human TLR1, TLR2, TLR3, TLR4, TLR6, TLR6, or TLR9). Only those cells containing human TLR3 showed marked expression of IFN-α/β, IL-6 or IL-12 when stimulated with poly (I):poly(C).

Mismatched dsRNA Induces Host Defense Gene Modulation through Highly Selective Activation of TLR3. To understand the relationship of the TLR3-dependent innate immune response to viral protection, Gowen (2007), subjected TLR3-deficient mice to dsRNA and measured expression of IFN-α/β, IL-6, and IL-12. The mice were also subsequently challenged by exposure to Punta Toro virus (PTV). Protection from the viral challenge was exquisitely sensitive to treatment with mismatched dsRNA. Viral protection conferred by mismatched dsRNA was completely abolished for the case of TLR3-deficient mice. When contrasted to the partial but significant effectiveness of mismatched dsRNA in $TLR3^{-/-}$ mice, it is clear that the structural substitutions of uridine in the cytidine strand of mismatched dsRNA are responsible for the highly specific, TLR3-dependent pathway. Furthermore, measurements of IFN-α/β and IL-6 directly link PTV protection or lack thereof to the modulation of these cytokines.

This selective targeting of the TLR3 signaling pathway represents a significant advantage for therapeutic applications of mismatched dsRNA as compared to other possible cytosolic mechanisms such as, for example, the use of unsubstituted dsRNA poly(I):poly(C) to stimulate cytokine production through RNA helicases such as MDA-5 and RIG-1 (Pichlmair, 2006).

(b) Binding of dsRNA to TLR3 Requires a Helical Non-Branching Conformation of dsRNA Molecular Model of the human TLR3 dimer ecodomain and its Rugged dsRNA ligand. The X-ray crystallographic structure of the mouse TLR3 dimer/dsRNA complex (3CIY) and the human TLR3 monomer (1ZIW) provided the coordinates for the model of human TLR3 with Rugged dsRNAbound to its active site (Liu, 2008; Bell, 2005). Molecular modeling used Accelrys' Discovery Suite software (version 2.5.5). The dsRNA structure of 3CIY was mutated in situ to the respective poly I and poly $C_{30}U$ chains (Rugged dsRNA) maintaining the phosphate backbone linear translational coordinates of the X-ray crystallographic structure that is represented as lines for its structure. A uridine in the poly $C_{30}U$ strand is at position U23. The coordinates of the human TLR3 monomer were used to replace each homodimer. Several unacceptable close van der Waals contacts for the human TLR3 crystal coordinates were resolved by an alternate rotamer conformation of the individual amino acid R group. The TLR3 homodimers are represented as structural elements with the blue arrows signifying direction of n-sheets and the red cylinders signifying α-helices. FIG. 24 is viewed from a lateral view of Rugged dsRNA bound to the active site of the TLR3 homodimer. The C-terminal regions of each dimer face each other and bind to the phosphate backbone of the dsRNA. The N-terminals of each TLR3 bind to opposite ends of the dsRNA with a minimum length of 50 bp required for interaction with essential residues of TLR3 for activation of intracellular signaling. Amino acids of TLR3 required for binding of Rugged dsRNA are shown as Van der Waals' radii associated with the phosphate backbone. FIG. 25 illustrates the TLR3 homodimer complexed with Rugged dsRNAas seen down the long axis of the dsRNA.

TLR3 Binding Site.

Studying the structure of native TLR3 crystals, Choe (2005) found that TLR3 is a large horseshoe-shaped, right-handed, solenoid structure comprised of 23 leucine-rich repeats. The glycosylated, convex surface and negatively-charged concave surfaces are unlikely binding sites for dsRNA. Consequently, they proposed that dsRNA binding occurs at positively-charged patches located on the lateral face.

Using mutational analysis, Bell (2005, 2006) modified putative TLR3 binding sites in the positively-charged patches and observed formation of a dsRNA/TLR3 complex by size-exclusion chromatography. Despite the presence of numerous positively-charged residues, only two amino acids N541 and H539 were required for binding. The amido group of H539 could interact with dsRNA by hydrogen binding. Proximity of the second positively-charged residue N541 was also important, albeit the role of this amino acid was not as clear. Mutation to negatively-charged aspirate prevented binding by dsRNA, however conversion to a neutral alanine residue had no effect on binding by dsRNA.

Binding to TLR3 Requires Helical Conformation of dsRNA.

Following the structural determination of most likely dsRNA binding surfaces on TLR3, Choe (2005) further proposed that the helical symmetry of dsRNA structure is necessary for the creation of the symmetric dimer form of activated, membrane-associated TLR3. In the ternary complex at the membrane surface, two symmetrically opposed TLR3 molecules are linked to either side of the helix of the common dsRNA.

As discussed above, using mutational analysis, Bell (2005, 2006) defined two highly conserved residues (N541 and H539) that are necessary for binding of dsRNA to TLR3. Moreover, the constraining requirement for ligand binding to both of these residues of TLR3 is satisfied only by the minor groove architecture of the (helical) conformation of dsRNA. When dsRNA phosphate binds in proximity to the charge sensitive H539, then the amide side (H541) becomes aligned with hydrogen bonding site of a 2' dsRNA hydroxyl only when helical dimensions are utilized.

(c) Helical Conformation of dsRNA and Alteration Thereto Accompanying Ligand Interactions Are Precisely Characterized by Circular Dichroism Circular dichroism provides detailed information concerning the secondary, helical structures of dsRNA or alterations thereof which accompany ligand binding; as well as structural changes caused by enzymatic hydrolysis and addition of metal ions. Also, in the thermal stress mode, conformational information imparted by CD provides valuable insights to explain RNA stability.

dsRNA Characterization.

Gray (1995) showed that CD, applied in the mixing curve protocol, complemented ultraviolet absorption measurements to determine the stoichiometry of duplex RNA (A-G: C-T(U)). In this approach, the optical property is analyzed as a function of the added ratios of individual strands. The magnitudes of CD difference plots were maximal for 50:50 mixtures. Further, isodichroic behavior correlated with the formation of higher ordered or intra strand structures.

Ligand Interactions.

Ghazaryan (2006) studied the ligand interaction of dsRNA with a family of positively charged pyridinium porphyrins. From CD measurements they found that minor modifications of porphyrin structure led to profound differences in mode of their attachment to the double helical structure. Whereas TEtOHPyP4 associated by intercalation, TMetAlPyP4 attached by forming an external, self-stacking assembly.

Using circular dichroism, Brown (2002) showed that ADAR1, a human dsRNA, (chimeric) converted from the A to Zα form upon binding to adenosine deaminase. Corroboration was provided by crystallization of the complex and Raman spectroscopy. Sorrentino (2003) studied the powerful enzymatic degradation of dsRNA by human pancreatic ribonuclease (HP-RNase). Circular dichroism of the RNA/enzyme complex revealed that multi-site attachment of the dsRNA to HP-RNase was responsible for the destabilization of the RNA helix.

Stability of dsRNA.

Studying the rRNA component of the 70S ribosomal complex, Sumita (2005) showed that pseudouridine substitutions stabilized the dsRNA helix based upon structural information provided by circular dichroism (CD). Specifically, pseudouridine substitutions created duplex regions with closing base pairs and water-mediated hydrogen bonds. Stabilization by Mg++ was also characterized by CD in this study. Investigating the stability of RNA-DNA hybrids with variants in base composition, Lesnik (1995) showed that more stable hybrids retain ellipticity at 210 nm, a wavelength characteristic of the single component RNA band (A-form hybrid). In contrast, less stable hybrids showed lowered 210 nm ellipticity, values which were intermediate between the RNA and DNA components.

Figure 1A:
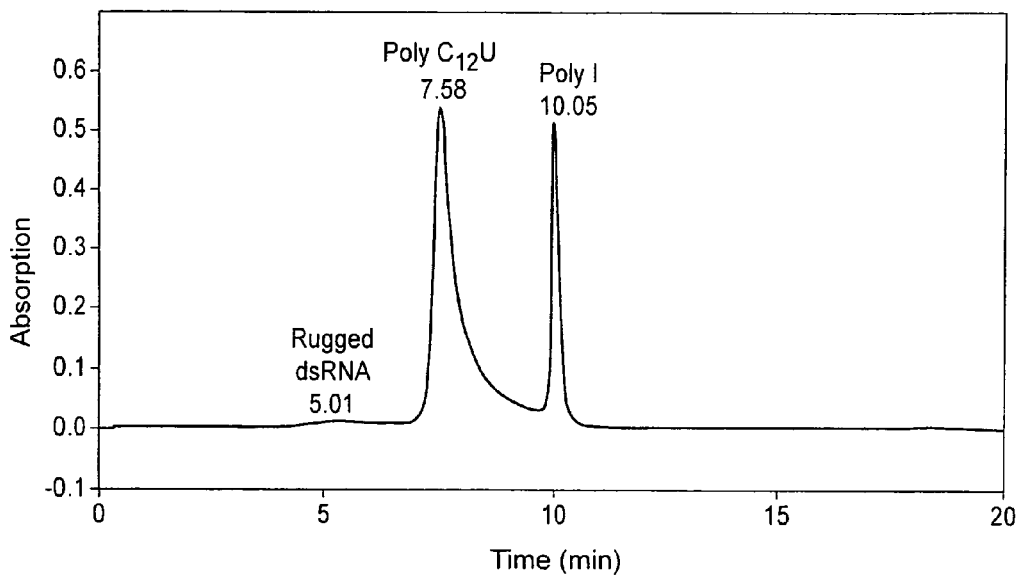
FIG. 1A shows an HPLC chromatogram for poly(I):poly($C_{12}U$). The minor peak (not integrated) centered at a retention time of about 5.00 min is Rugged dsRNA. The first major peak centered at a retention time of about 7.58 min is the single-stranded poly($C_{12}U$). The second major peak centered at a retention time of about 10.05 min is the single-stranded poly(I). The molecular identity of each peak was determined by photodiode array (PDA) analysis.
Figure 1B:
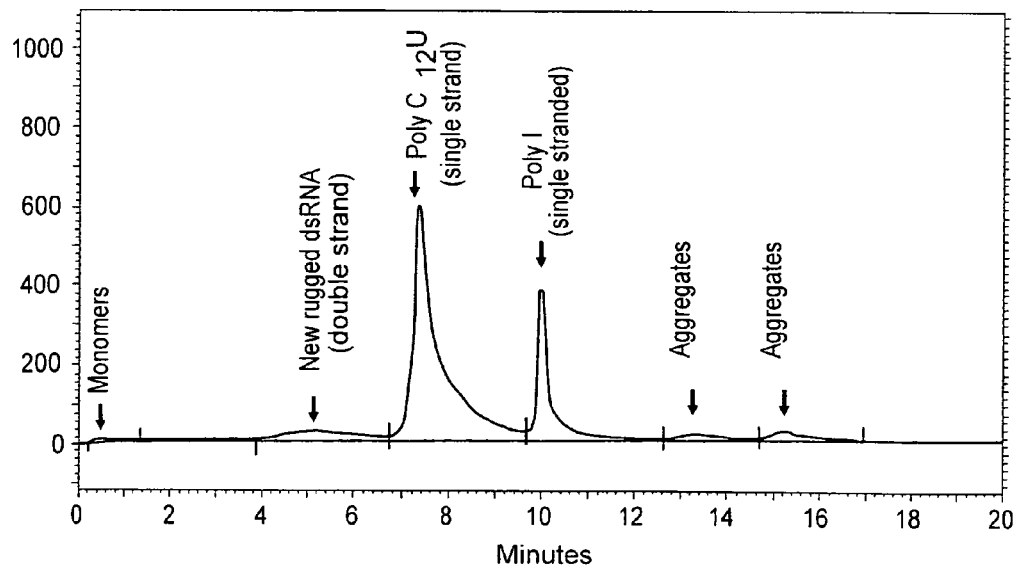
FIG. 1B is an HPLC chromatogram for lyophilized poly (I):poly($C_{12}U$) showing aggregates lyophilization can produce. Note that aggregation does not occur in the solution process of FIG. 10, which avoids lyophilization.
Figure 1C:
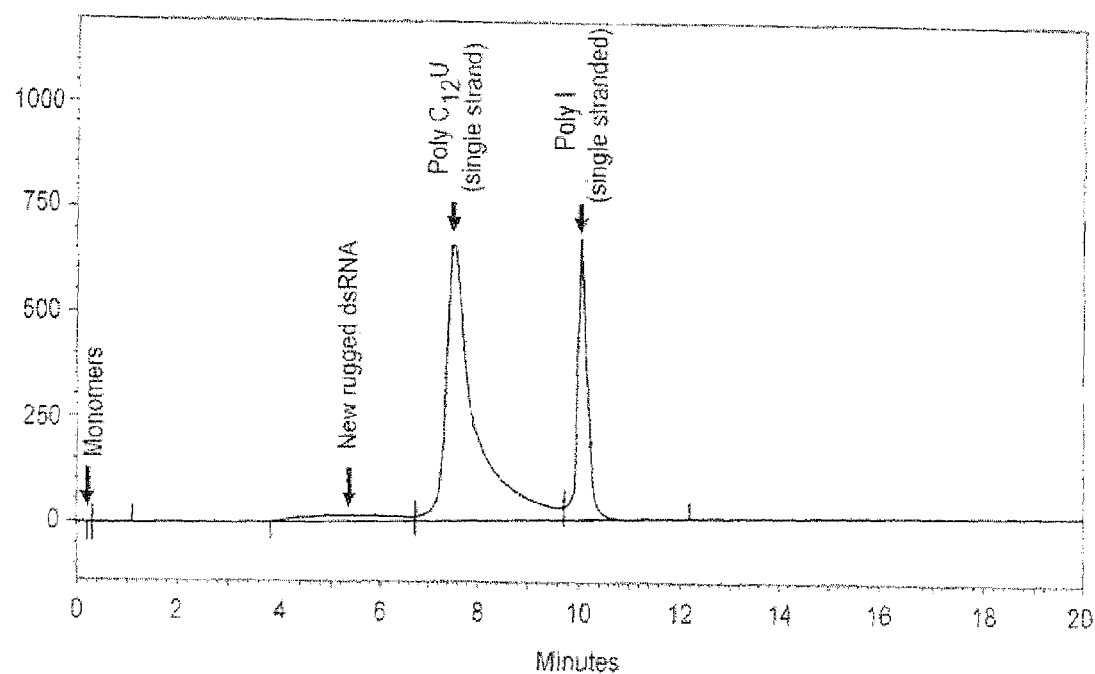

A double-stranded RNA composition may be analyzed by high performance liquid chromatography (HPLC) as shown in FIGS. 1A, 1B and 1C. Analysis of a representative lot of Ampligen® poly(I):poly($C_{12}U$) mixture resulted in two distinct peaks: one with retention times from 9.85 to 10.35 min corresponding to the poly(I) strand and from 7.30 to 7.80 min corresponding to the poly($C_{12}U$) strand. Rugged dsRNA is found at a retention time of about 5 min representing a molecular species uniquely resistant to denaturation and unfolding. Denaturing conditions would eliminate biological activity exclusively due to TLR3 receptor binding. This analytical method may also be used as a stability indicating assay and, in particular, it may be used to show that the Rugged dsRNA is unusually resistant to disruption of its double helix and to molecular unfolding.

For the lyophilized (freeze-dried) preparation (FIG. 1B), aggregates may be present and elute at 13 and 15 min. A small fraction of individual nucleosides, inosine, cytosine and uridine, elute at 1 min. The overall purity of poly I:poly$C_{12}U$ (Ampligen®) determined by HPLC is represented by the sum of the 7.4, 8.7 and 10 minute peaks and is 96-99%. "New dsRNA" comprises 1-4% and is different from Ampligen® by its size and physico-chemical properties as discussed herein.

Figure 2A:
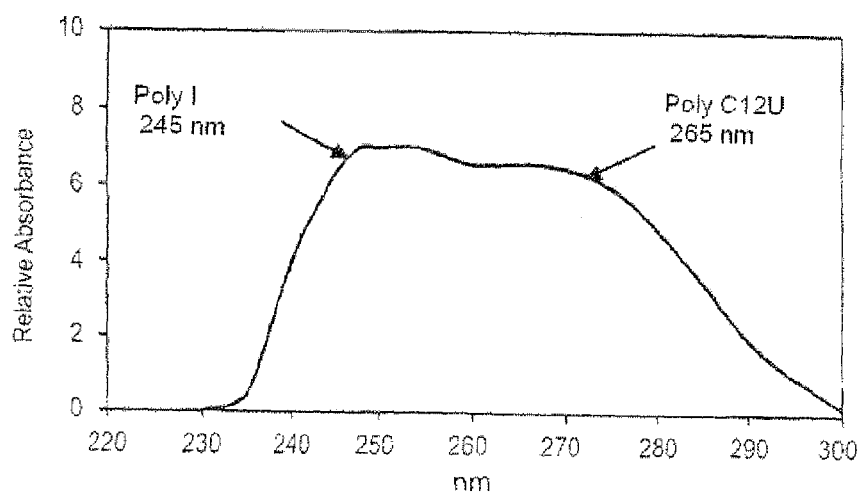
FIG. 2A is FDA analysis of the peak centered at a retention time of about 5.01 min, which contains both poly(I) and poly($C_{12}U$) character.
Figure 2B:
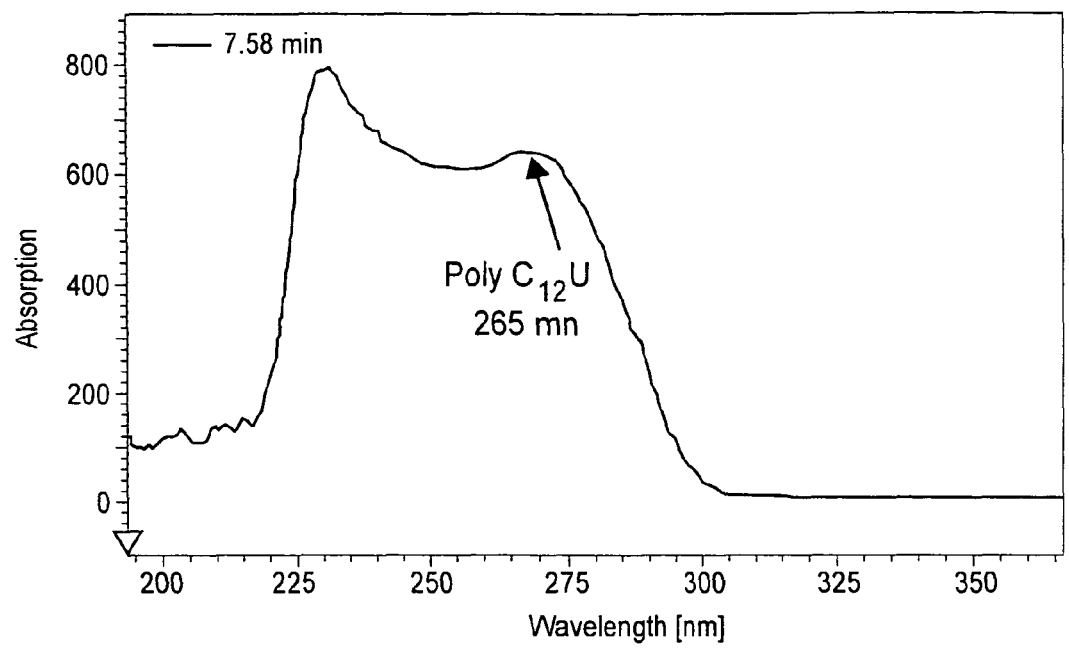
FIG. 2B is PDA analysis of the peak centered at a retention time of about 7.58 min, which contains poly($C_{12}U$).
Figure 2C:
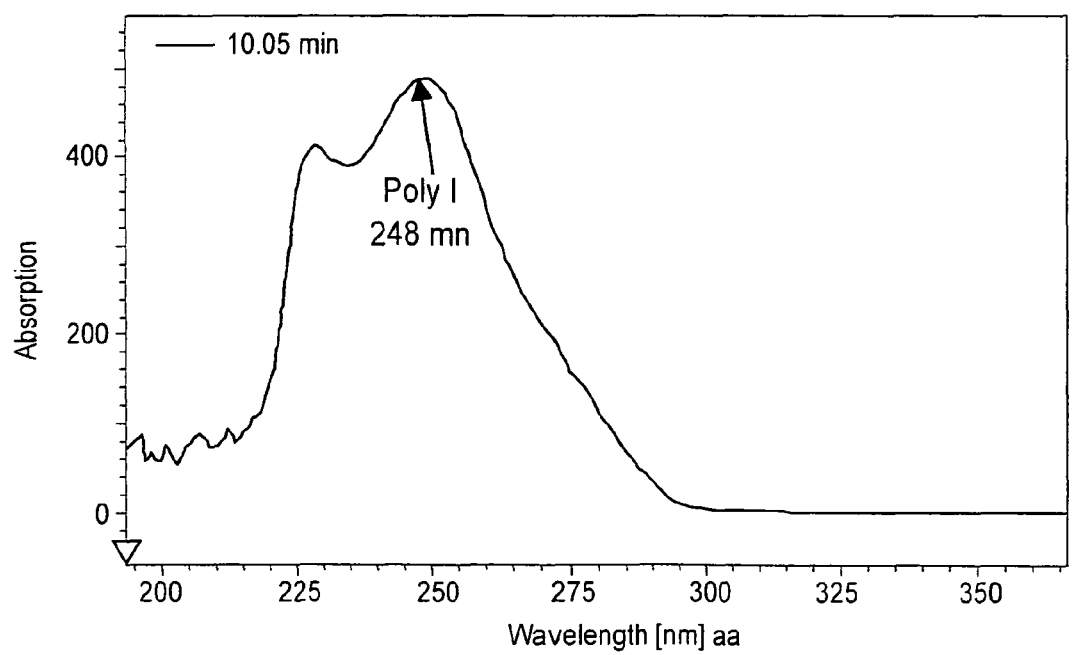
FIG. 2C is PDA analysis of the peak centered at a retention time of about 10.05 min, which contains poly(I).
Figure 3:
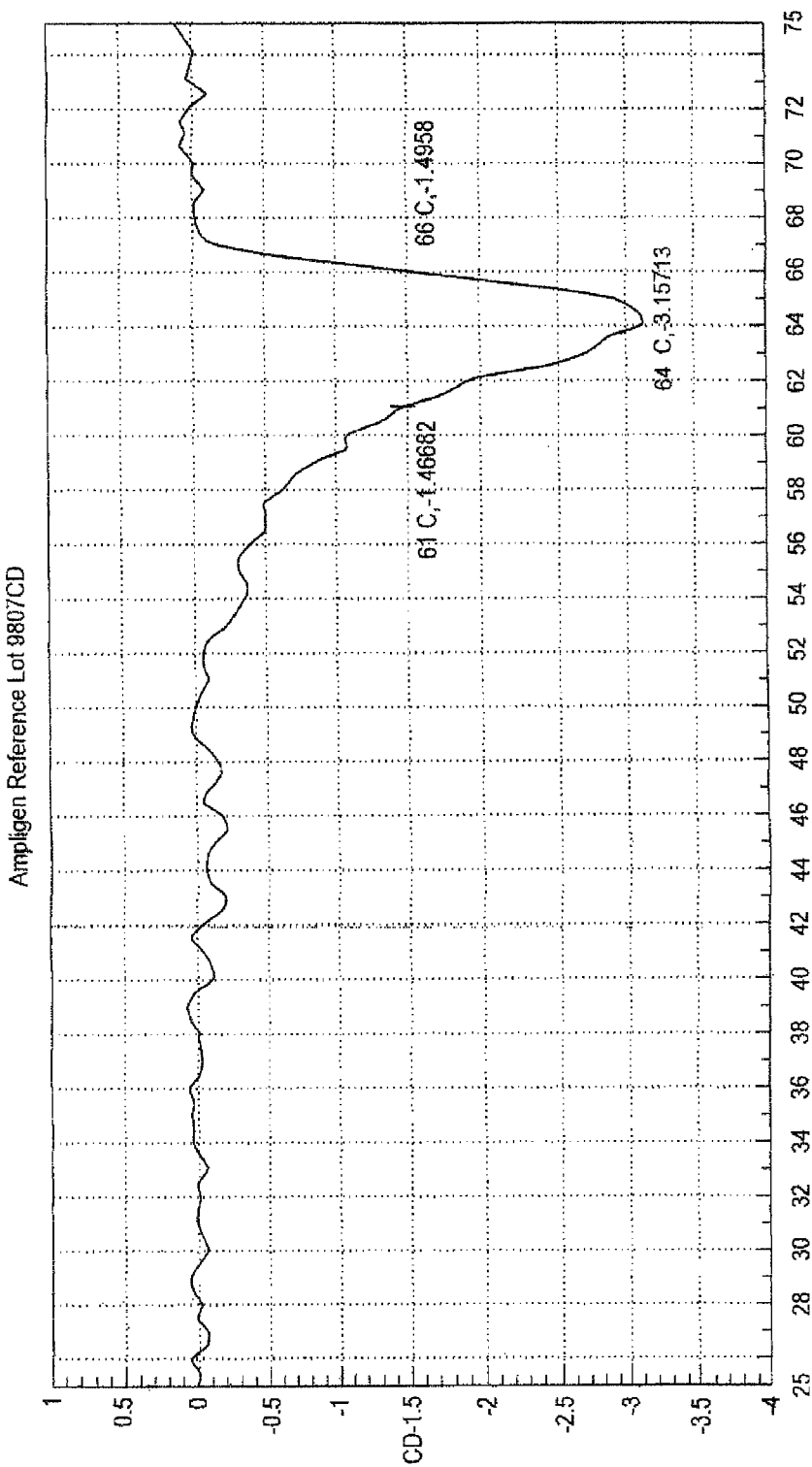
FIG. 3 is a circular dichroism (CD) of poly (I):poly ($C_{12}U$). The melting point of 64° C. represents the condition of ½ double stranded structure.

The identity of each peak is determined by analysis with a photodiode array (FDA) detector as shown in FIGS. 2A, 2B and 2C. At each selected retention time, a UV absorption scan of wavelengths from 200 nm to 360 nm was obtained. Duplex poly(I):poly($C_{12}U$) and individual poly(I) and poly($C_{12}U$) strands have their own specific peak absorption wavelengths. Absorption peaks centered at both 248 nm and 265 nm indicate the presence of Rugged dsRNA (about 286,000 daltons) having poly(I) and poly($C_{12}U$), respectively (FIG. 2A). Peak absorption centered at about 265 nm indicates the presence of the poly($C_{12}U$) strand (FIG. 2B). Peak absorption centered at about 248 nm indicates the presence of the poly(I) strand (FIG. 2C). Absorption centered at about 230 nm is due to acetonitrile used as solvent. Because of the relative scarcity of Rugged dsRNA, the signal at 230 nm was subtracted from FIG. 2A.

FIG. 21 shows the relative size of Ampligen® vs new Rugged dsRNA (peak 5 minutes)

Figure 22:
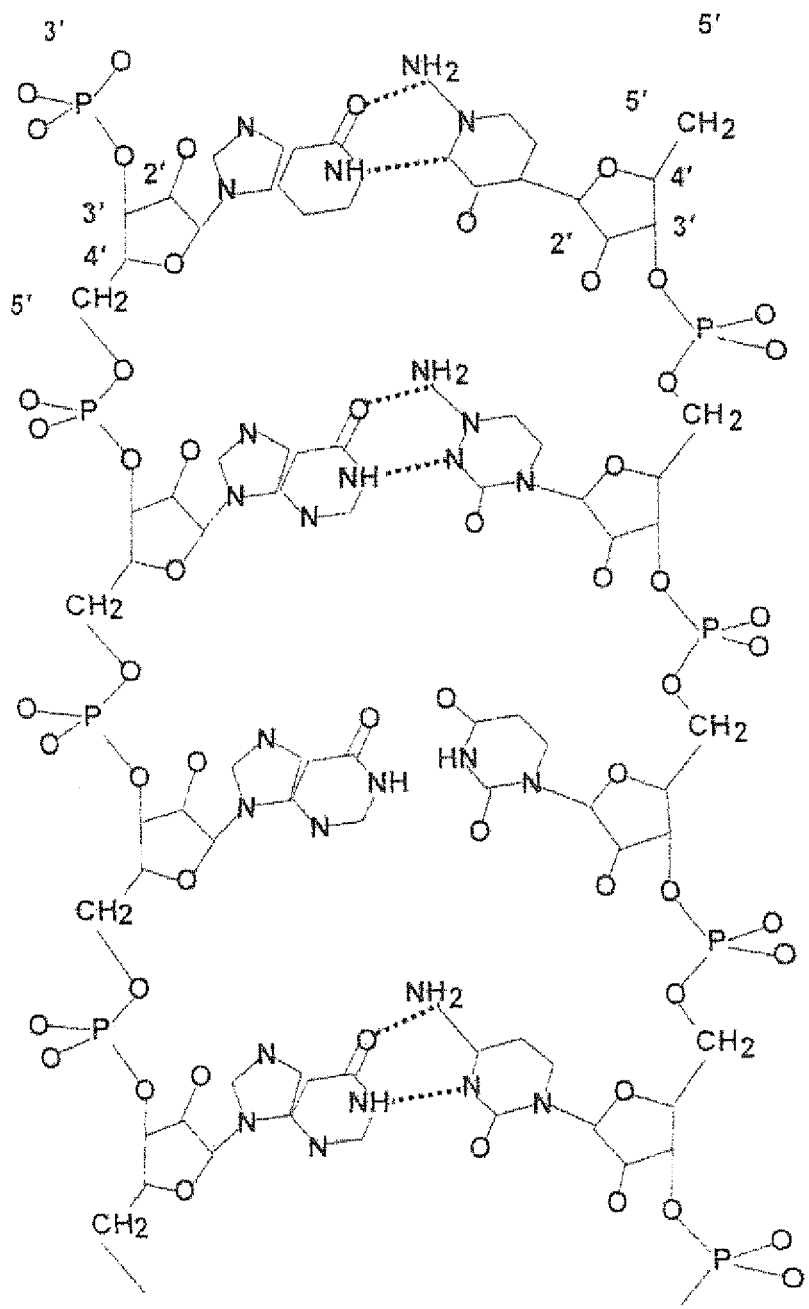
FIG. 22. Partial view of poly(I):poly($C_{12}U$) partially hybridized strands and the interaction of bases of individual poly(I) and the poly ($C_{12}U$) strands. Molecular weight 1,100,000 da.

Shown in FIG. 22 is a partial view of poly(I):poly($C_{12}U$) partially hybridized strands and the interaction of bases of individual poly(I) and the poly($C_{12}U$) strands. Single inosine bases bind to cytosine bases, but not to the uridine base. In this structure, the poly (inosinic acid) is hydrogen bonded (dashed lines between bases) to poly (cytidylic acid), with uridylic acid substitution occurring on an average of every 12-13 bases.

Molecular formula: $(13C_{10}H_{11}N_4O_7P)_n$: $((12C_9H_{12}N_3O_7P)(C_9H_{11}N_2O_8P))_n$ Molecular size: about 1,200,000 daltons The number of repeat units (n) corresponding to the size of poly(I):poly($C_{12}U$) of approximately 1.2 Mda is 2000 base pairs or 187 full helical turns.

TABLE 2

Molecular Weight (MW) of Unimproved Ampligen ® Mixture Components.
Common name: poly(I):poly($C_{12}U$) (1,200,000 daltons)
Chemical name: poly(inosinic acid):poly((cytidylic acid)$_{12}$(uridylic acid))

| | MW | Unit | Unit MW* |
|---|---|---|---|
| Inosine 5' mono-phosphate | 330 | 13 | 4056 |
| Cytidine 3' mono-phosphate | 305 | 12 | 3444 |
| Uridylic acid | 306 | 1 | 288 |
| Overall | Average: 318 | | Sum: 7788 |

Figure 23:
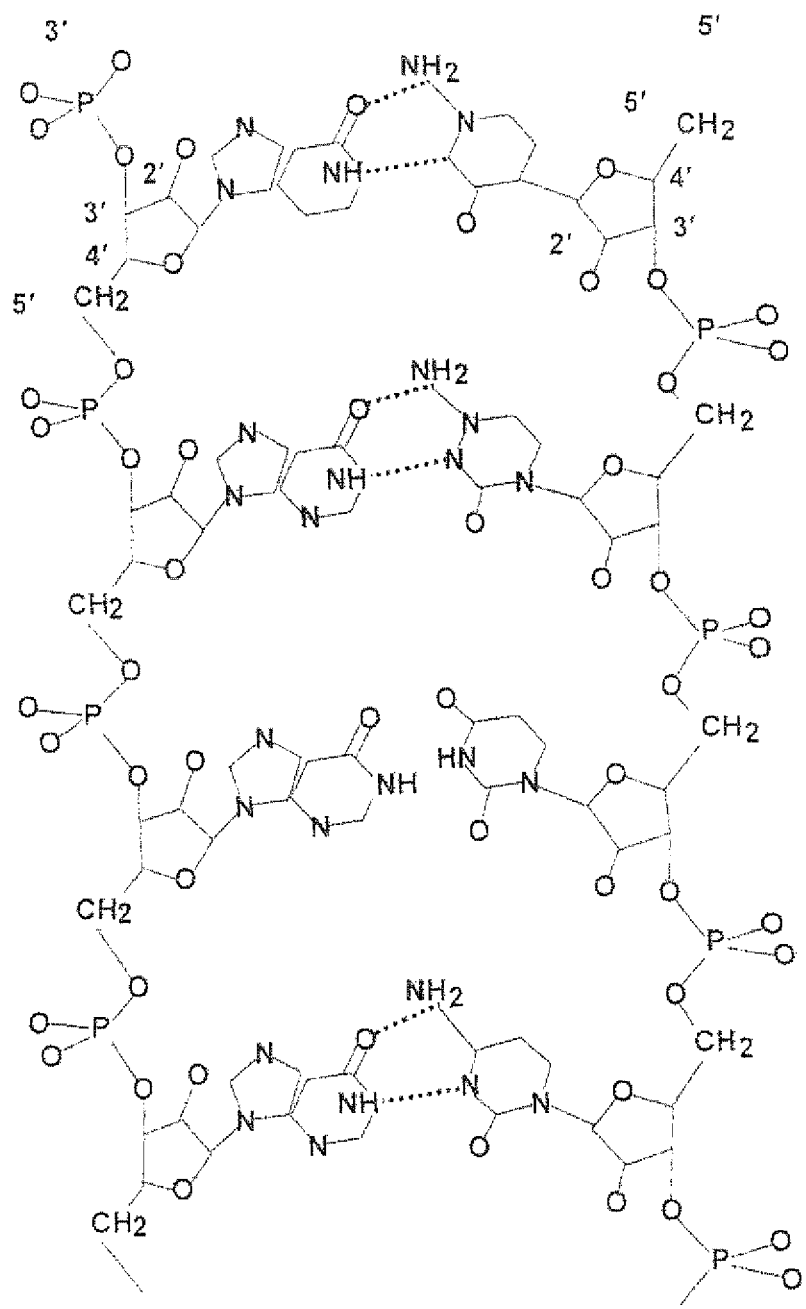
FIG. 23. Partial view of poly(I):poly($C_{12}U$) partially hybridized strands and the interaction of bases of individual poly(I) and the poly ($C_{12}U$) strands. Molecular weight 286,000 da.

*Note:
One molecule of $H_2O$ (mw = 18) is lost for each phosphodiester bond formed Shown in FIG. 23 is a partial view of Rugged dsRNA, poly(I):poly($C_{30}U$), partially hybridized strands and the interaction of bases of individual poly(I) and the poly($C_{30}U$) strands. Single inosine bases bind to cytosine bases, but not to the uridine base. In this structure, the poly (inosinic acid) is hydrogen bonded (dashed lines between bases) to poly (cytidylic acid), with uridylic acid substitution occurring on an average of every 30-31 bases. This is "rugged" dsRNA.

Molecular formula: $(31C_{10}H_{11}N_4O_7P)_n$: $((30C_9H_{12}N_3O_7P)(C_9H_{11}N_2O_8P))_n$ Molecular size: about 300,000 daltons The number of repeat units (n) corresponding to the size range of new variant, also termed Rugged dsRNA (also termed peak 5 min on HPLC) is about 30-300 Kda having about 50-500 base pairs representing 4.7-46.7 complete turns of RNA helix and is resistant to disassembly of hydrogen-bonded strands under elevated thermal or abnormal ionic conditions.

TABLE 3

Molecular Weight (MW) of Novel Rugged dsRNA Components.

| | MW | Unit | Unit MW* |
|---|---|---|---|
| Inosine 5' mono-phosphate | 330 | 31 | 9,672 |
| Cytidine 3' mono-phosphate | 305 | 30 | 8,610 |
| Uridylic acid | 306 | 1 | 288 |
| Overall | Average: 318 | | Sum: 18,570 |

*Note:
One molecule of $H_2O$ (mw = 18) is lost for each phosphodiester bond formed Circular dichroism (CD) has been used to measure secondary structure (duplexed helices) of biological and synthetic polymers, including proteins and nucleic acids. CD is the measurement of absorption of right- or left-circular polarized light, at a specific wavelength, by chiral molecules. Chemical chirality is the property of a molecule being nonsuperimposable on its mirror image. An atom that makes its molecule chiral is called a chiral atom or, more commonly, a chiral center. Rugged dsRNA and Poly(0:poly($C_{12}U$) have a number of chiral centers because of their primary and secondary structures. Chiral centers are found in the nucleotide bases, which form the two primary structures for the two individual RNA strands (ssRNA) of Rugged dsRNA and poly(I):poly ($C_{12}U$). Additional chiral centers come from hybridizing each ssRNA to the other through hydrogen bonding of their complementary bases. Hydrophobic bonding between adjacent bases of dsRNA is known as base stacking and produces a flexible, linear symmetrical, helical secondary structure of defined shape and size. CD spectra for Rugged dsRNA and Ampligen®, which are dependent on the wavelength, are observed to be a function reflecting the Gaussian absorption for each chiral center. Therefore, the CD spectrum for a dsRNA such as Rugged dsRNA is dependent on the complementary base pairing of double-stranded structures and the complex chirality of the resultant helical structure.

It has been demonstrated by UV and CD spectroscopy that the biological activity of dsRNA is dependent on these specific spatial and steric configurations. Since perturbation of helical structure results in loss of the chiral centers characteristic of the secondary structure, the analysis and monitoring of secondary structure by CD provides a method to characterize the physico-chemical properties of Rugged dsRNA and poly(I):poly($C_{12}U$) that are associated with their bioactivity.

The specific ellipticity measured in a wavelength scan provides a quantitative parameter, which is calculated as the ellipticity ratio at certain "critical" wavelengths. The value of this structural parameter, the ratio $CD_{278}/CD_{245}$, is a characteristic of Rugged dsRNA or the unimproved Ampligen® mixture. In a second CD analysis, ellipticity is measured during heating. As poly(I):poly($C_{12}U$) is heated and thermally denatured, the individual poly(I) and poly($C_{12}U$) strands unwind due to the breakdown of hydrogen bonding between complementary base pairs. When the temperature derivative of ellipticity is plotted, the minimum derivative value corresponds to melting temperature, defined as the point where 50% of the double-stranded conformation is unwound. The width at half-height of the peak, a measure of structural uniformity, also becomes an indication of its integrity. Taken together, these thermal indices provide a measure of the strength of the dsRNA helixes.

Figure 4:
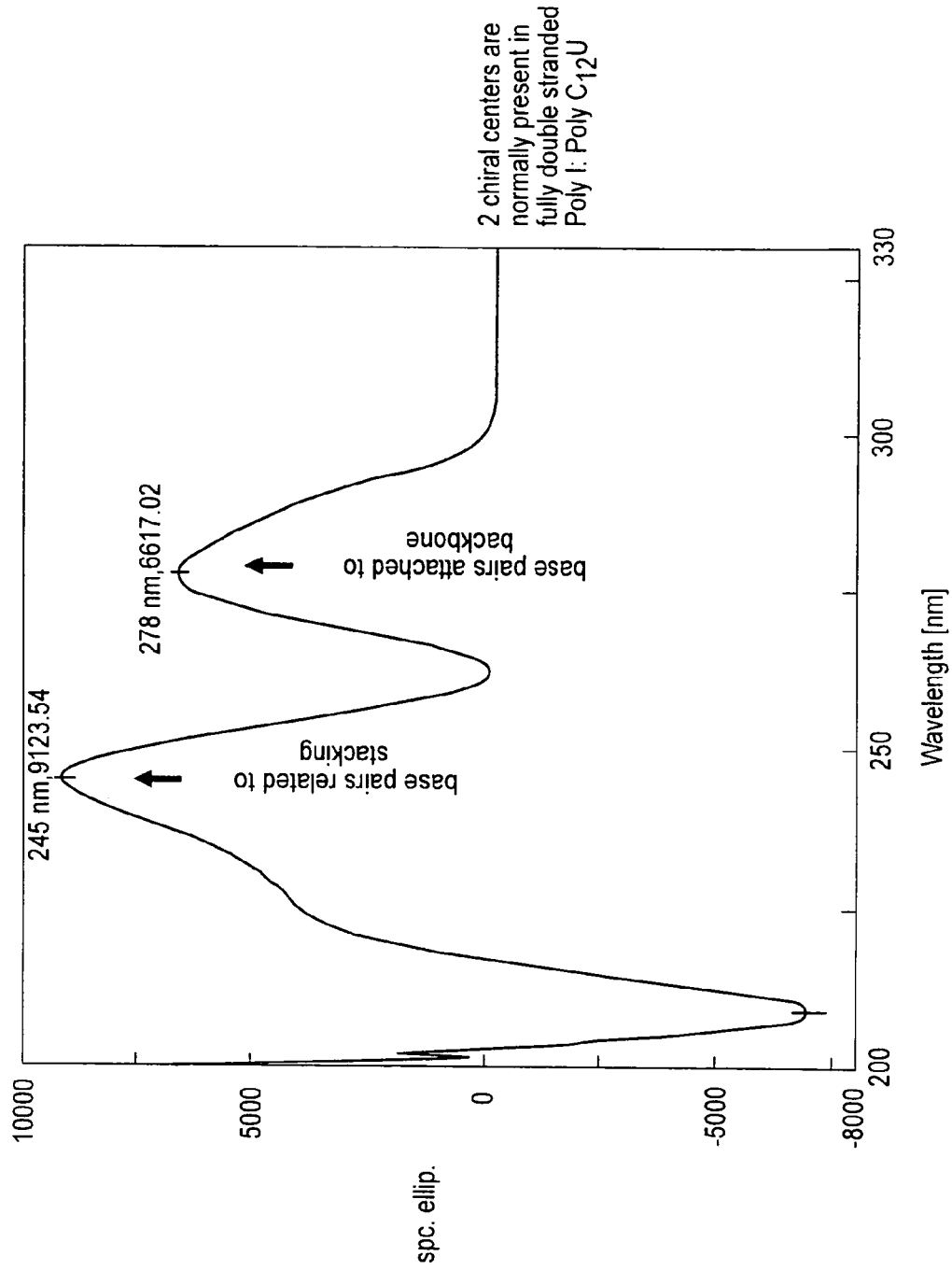
FIG. 4 is the CD wavelength scan of poly (I):poly ($C_{12}U$). The double stranded structure is characterized by two peaks at 245 nm and 278 nm, representing two chiral centers normally present in fully double stranded poly I:poly ($C_{12}U$). These centers represent chirality due to base pair structure (278 nm) and the base stacking which is associated with the formation of duplex double helix.
Figure 5:
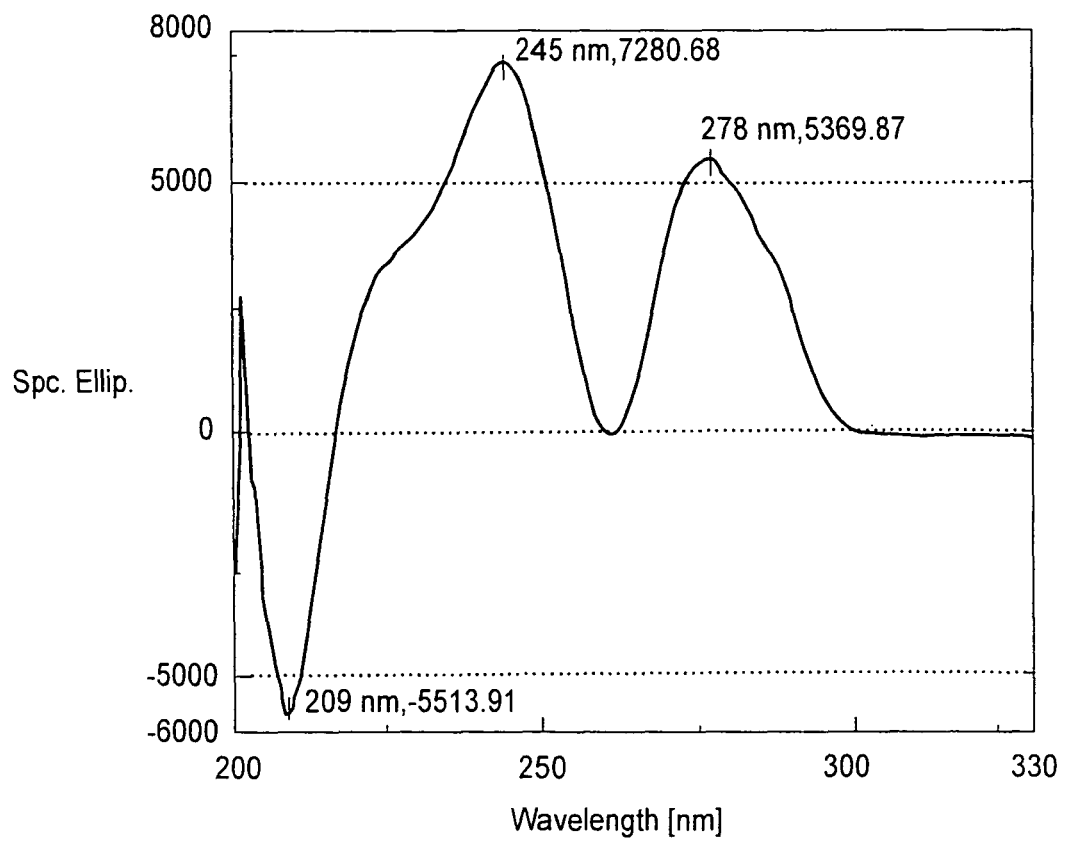
FIG. 5 shows the circular dichroism of poly (I):poly ($C_{12}U$) with the characteristic chiral peaks at 245 nm and 278 nm
Figure 6:
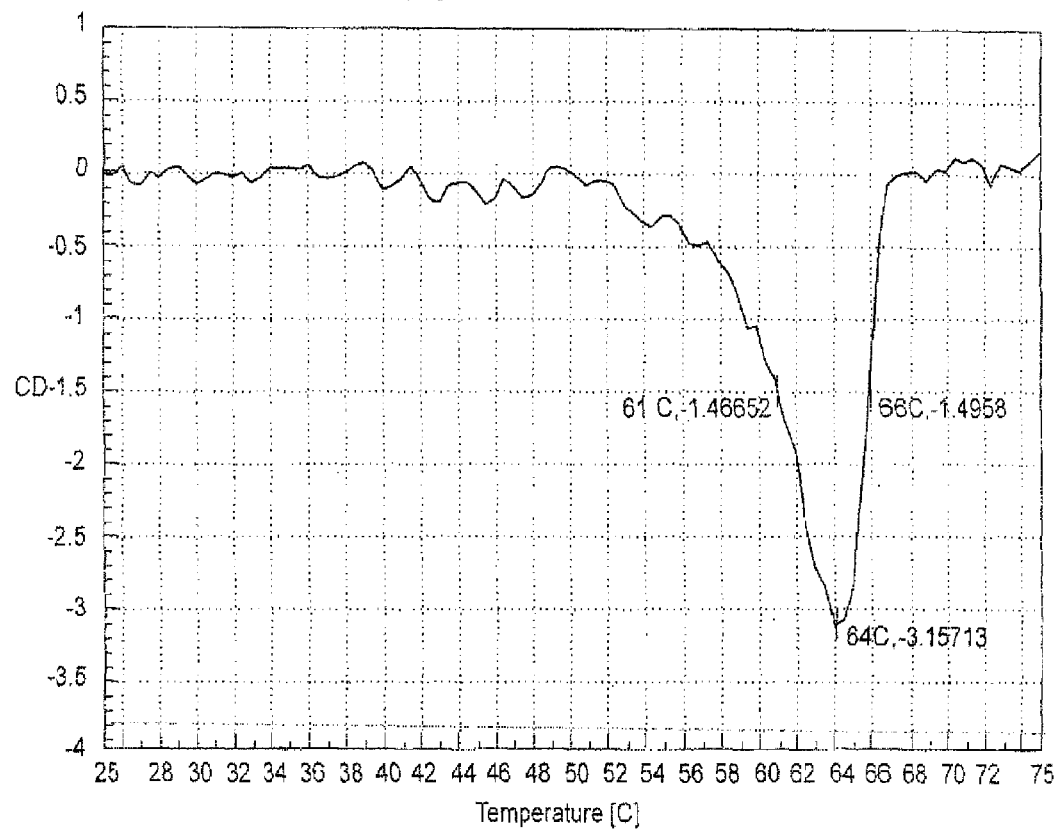
FIG. 6 shows a plot of the derivative of the thermal melt of poly (I):poly ($C_{12}U$). Integrity of the structure is characterized by the melting point and the ½ width of this derivative profile, both expressed as degrees C.

The wavelength scan detects two peaks: a first peak at 245 nm corresponding to the doubled stranded helix of the poly (I):poly($C_{12}U$) and a second peak at 278 nm corresponding to the stacking of the nucleic acid's base pairs. As shown previously in FIGS. 4 and 5, dsRNA affords separate peaks in the CD wavelength scan, at 245 and 278 nm, the former peak associated with base stacking attribute of helical structure. Accordingly, the ratio of peak heights at 278/245 is typically within 0.69-0.79 for dsRNA but much higher in the absence of double helical structure.

Table 4 summarizes CD wavelength scans obtained by isolation of fractions of the three reversed phase HPLC peaks previously discussed in FIGS. 1B and 1C. The reversed phase HPLC assay is utilized to distinguish "rugged" dsRNA (5.0 minute peak) from the separated, component strands of poly (I):poly($C_{12}U$): 7.0 (poly $C_{12}U$) and 10.0 minute peaks (poly I). It is clear from the 278/245 ratio that only the 5.0 minute, Rugged dsRNA fraction retains helical structure, in contrast to the separated, component strands of Poly I:Poly $C_{12}U$.

This result underscores the greater stability of Rugged dsRNA during the reversed phase isolation, in which all polynucleotides experience binding and elution. Whereas poly(I):poly($C_{12}U$) is separated into the component 7 and 10 minute polynucleotide strands, the 5 minute, Rugged dsRNA, retains the double stranded conformation.

TABLE 4

PREPARATIVE HPLC*:
Peak Analysis by Circular Dichroism

| Lot | Peak (min) | Circular Dichroism 278/245 nm response requirement (0.69-0.79) |
|---|---|---|
| 0303SD | 5 Min | 0.78 |
| | 7 min | 12.3 |
| | 10 min | 1.74 |

TABLE 4-continued

| | | |
|---|---|---|
| 0301SD | 5 Min | 0.79 |
| | 7 min | 2.49 |
| | 10 min | N/A |

*Preparative HPLC Methodology:

| | |
|---|---|
| HPLC Equipment: | Beckman Coulter Preparative HPLC (System Gold 126P Solvent Module), Beckman coulter (System Gold 168 Detector) |
| Column: | Phenomenex, Polymerx, 10μ, RP-1, 100° A, 250 × 21.20 mm |
| Mobile Phase: | 200 mM of Triethylamine Acetate buffer, pH 8.7 |
| Flow Rate: | 5.0 mL/minute |
| Injection Volume: | 5 mL |
| Wavelength: | 255 nm and photodiode array detection. |

TABLE 5

Gradient Condition:

| Time (Minute) | Acetonitrile (%) | Buffer (%) |
|---|---|---|
| 0 | 8 | 92 |
| 3 | 10 | 90 |
| 6 | 12 | 88 |
| 9 | 14 | 86 |
| 12 | 16 | 84 |
| 14 | 20 | 80 |
| 30 | 20 | 80 |

The column was equilibrated with 8% acetonitrile and 92% buffer for at least 30 minutes. Peaks were collected at 10-12 minutes and 22-27 minutes which corresponded to differing gradient acetonitrile compositions indicated in Table 5 above. The injection process was repeated 20-30 times and fractions from the first peak (10-12 minutes) were pooled for subsequent analysis.

The pooled fractions were concentrated and solvent was displaced with a water wash, using Amicon Ultra Centrifugal Filters (Amicon Ultra, Cat UFC 50104). The concentrated samples were analyzed for concentration by UV, based upon averaging of the concentration responses which were separately calculated at the wavelength maximum for each polynucleotide chain: $\epsilon=5.2\times10^3$ at $\lambda=265$ nm and $\epsilon_2=4.9\times10^3$ at $\lambda=249$ nm.

Only 5 minute exhibits double stranded base stacking character:

Significant 245 nm response reflecting double strand helix (245 nm)

Acceptable 245/278 Ratio reflecting base pairs=278 nm (chiral centers in backbone).

Precision.

Ampligen® poly(I):poly($C_{12}U$), lot 9807CD, at a concentration of 2.5 mg/mL was repeatedly assayed to investigate the precision of the CD assay. The percent relative standard deviations (% RSD) for the melting temperature ($T_M$), for the width at half-height for the first derivative of the melting curve and for the ratio of measurements of the CD peaks at 278 nm and 245 nm were calculated as 0.76%, 9.09%, and 1.41%, respectively. This demonstrated that CD assay of Ampligen® poly(I):poly($C_{12}U$) acts in a precise manner during thermal analysis for the determination of $T_M$ and width at half height of the first derivative of the thermal melt curve and during the CD scan analysis for determination of the ratio of CD at 278 nm to CD at 245 nm.

Specificity.

Figure 7:
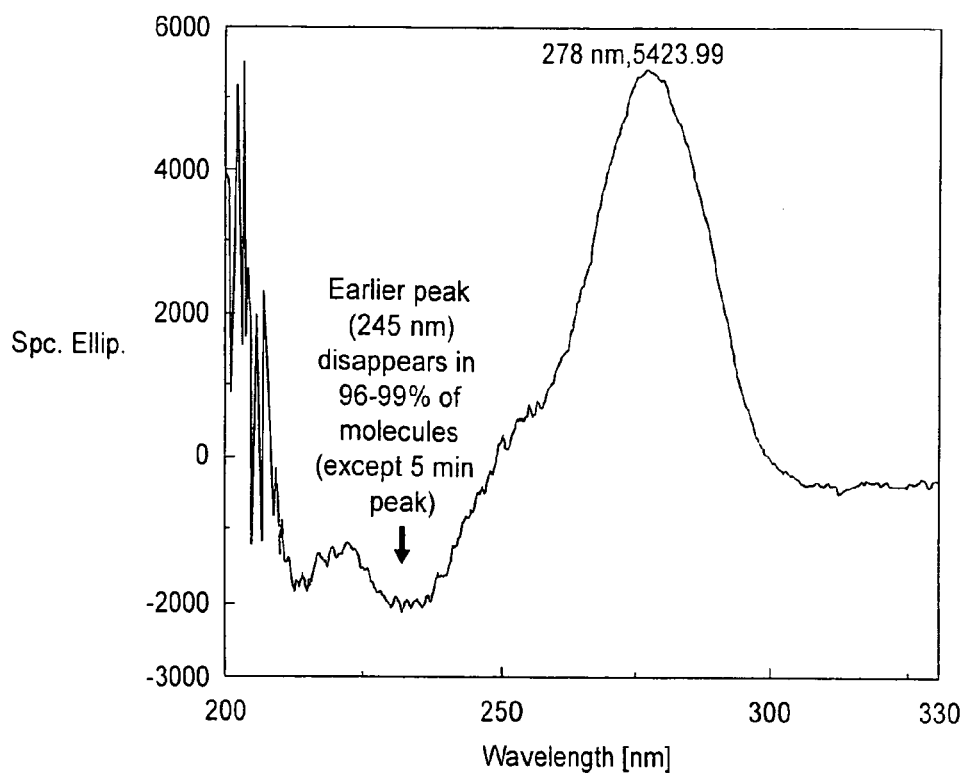
FIG. 7 shows by HPLC that preparation with heating abolishes all double strand structure as reflected by loss of 245 nm peak seen in FIG. 4 since the 245 nm peak is due to chiral base stacking. However, analysis by circular dichroism shows that, as a product of thermal stress, the 5 minute peak maintains both double helix configuration and chiral centers in the backbone.
Figure 8:
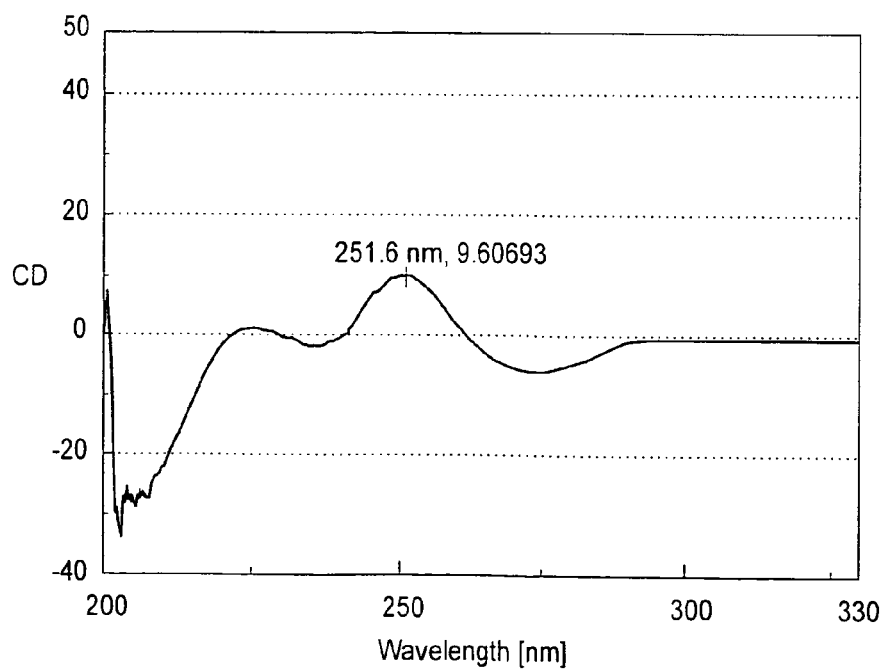
FIG. 8 shows a CD plot of a thermal melt of single stranded poly (I). The chiral center for inosine provides a weak signal at about 252 nm.
Figure 9:
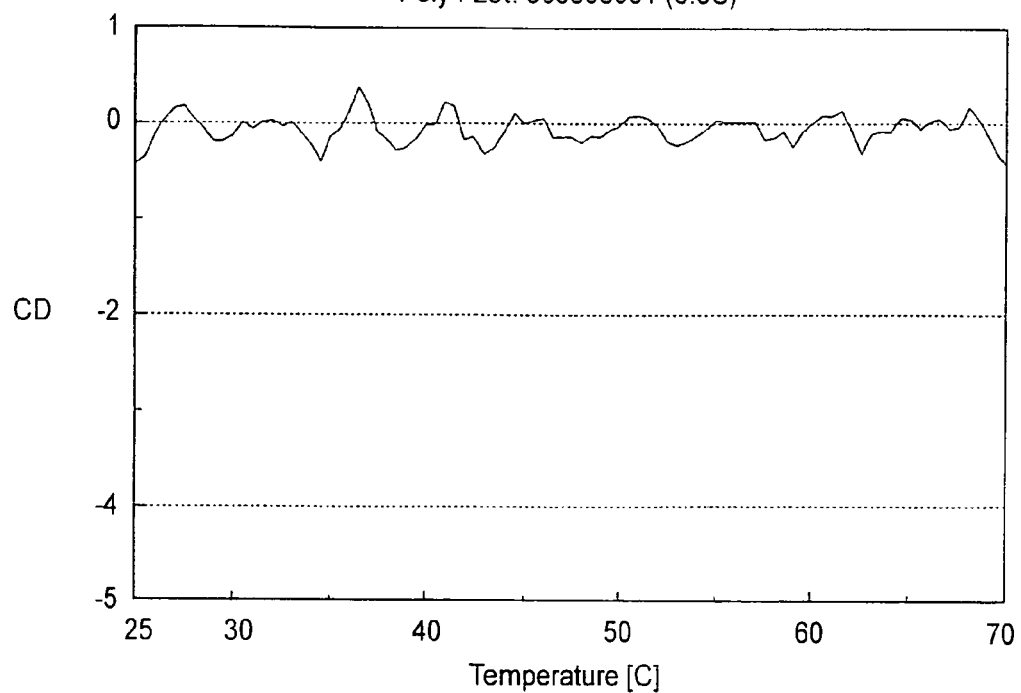
FIG. 9 shows a plot of the derivative of the thermal melt of single stranded poly (I) There is no evidence of intra molecular base stacking at thermal condition which would otherwise disrupt a double helix.

This CD method for characterizing poly(I):poly($C_{12}U$) is also specific because it can between differentiate duplexed nucleic acids and single-stranded nucleic acids, or other similar double-stranded nucleic acids that do not meet the manufacturing and release specifications for Ampligen® poly(I):poly($C_{12}U$). The specificity of this method, in regards to analysis of single versus double-stranded nucleic acids, was demonstrated by comparing scanning profiles and melting temperature curves. See FIG. 7. The scans of double-stranded molecules such as poly(I):poly($C_{12}U$), poly(I):poly(C), and poly(A):poly(U) differed significantly from those obtained during analysis of single-stranded molecules such as poly(I) and poly($C_{12}U$). See FIGS. 8-17. Furthermore, each of the CD scans was unique for the molecular species being assayed.

The specificity of the assay was also investigated to assess, unequivocally, the ability to detect compounds of closely related structure.

Figure 10:
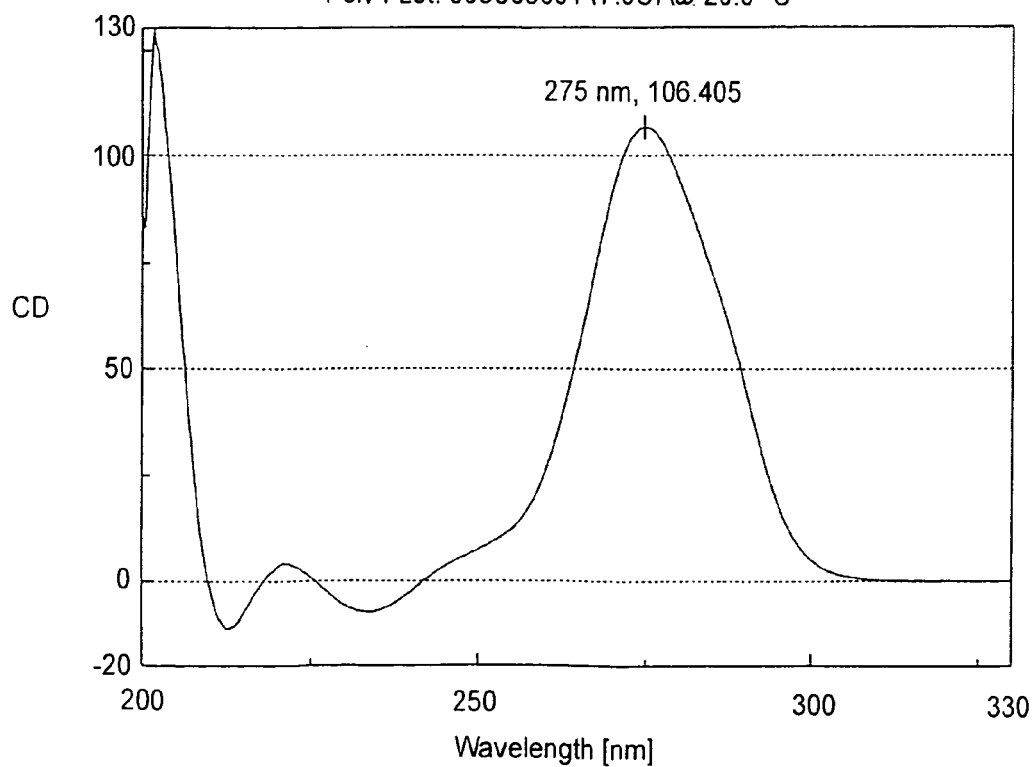
FIG. 10 shows a HPLC chromatogram of a sterile solution of poly I: poly ($C_{12}U$) also showing a novel 5 minute peak.
Figure 11:
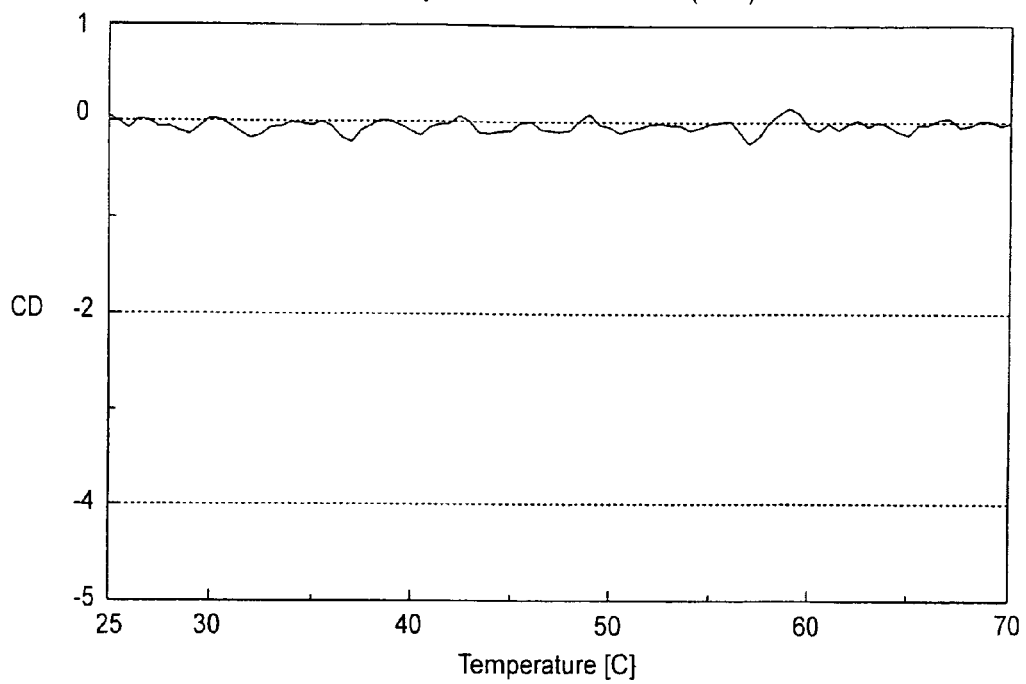
FIG. 11 shows a plot of the derivative of the thermal melt of single stranded poly ($C_{12}U$). There is no evidence of intra molecular base stacking at thermal condition which would otherwise disrupt a double helix.
Figure 12:
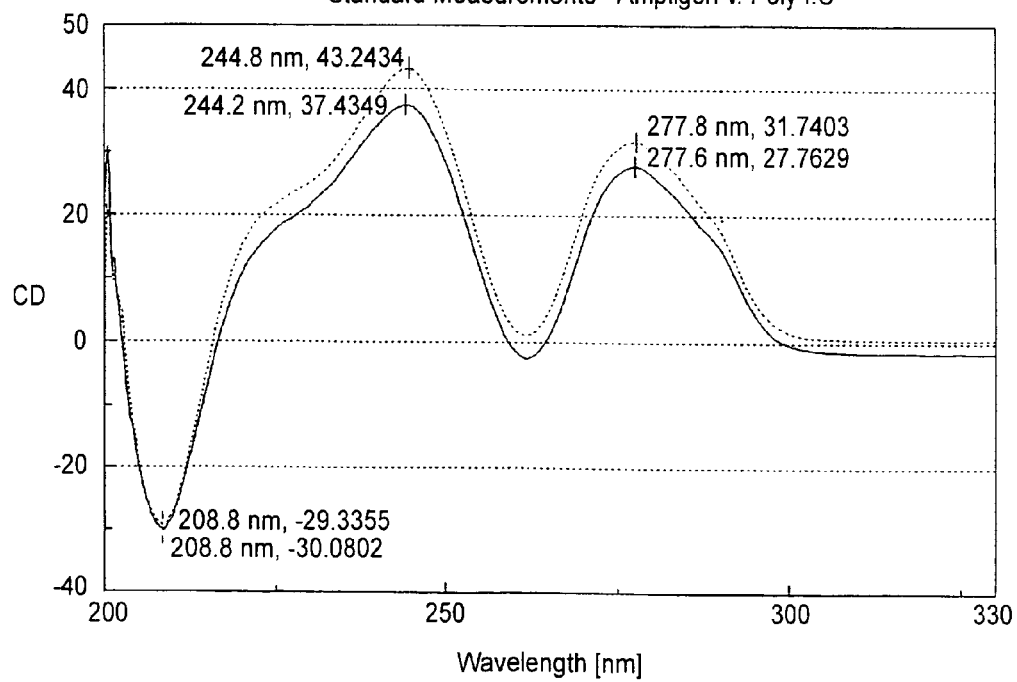
FIG. 12 shows a CD plot of a thermal melt of poly(I):poly ($C_{12}U$) and poly (I):poly (C). Base stacking is evident in both compounds as indicated by the peak at 245 nm.
Figure 13:
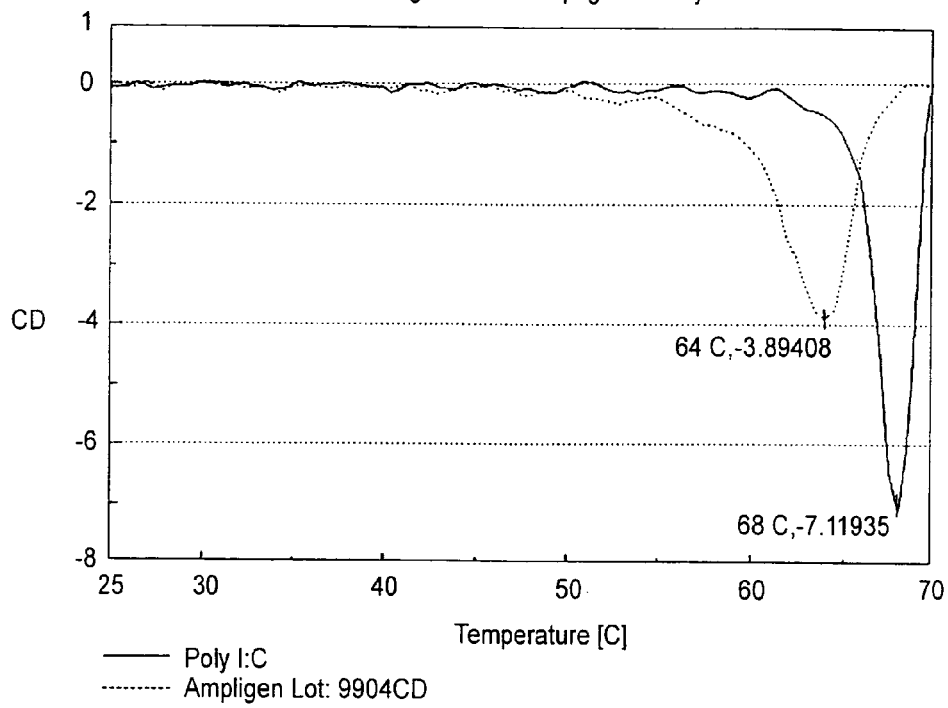
FIG. 13 shows a plot of the derivative of the thermal melt of poly(I):poly ($C_{12}U$) and poly (I):poly(C). Both compounds exhibit the critical melting point for disruption of the double helix. However, the lower melting point of Poly I:Poly $C_{12}U$ illustrates a more labile character which in turn affords the advantageous safety profile of the uridine substituted compound.
Figure 14:
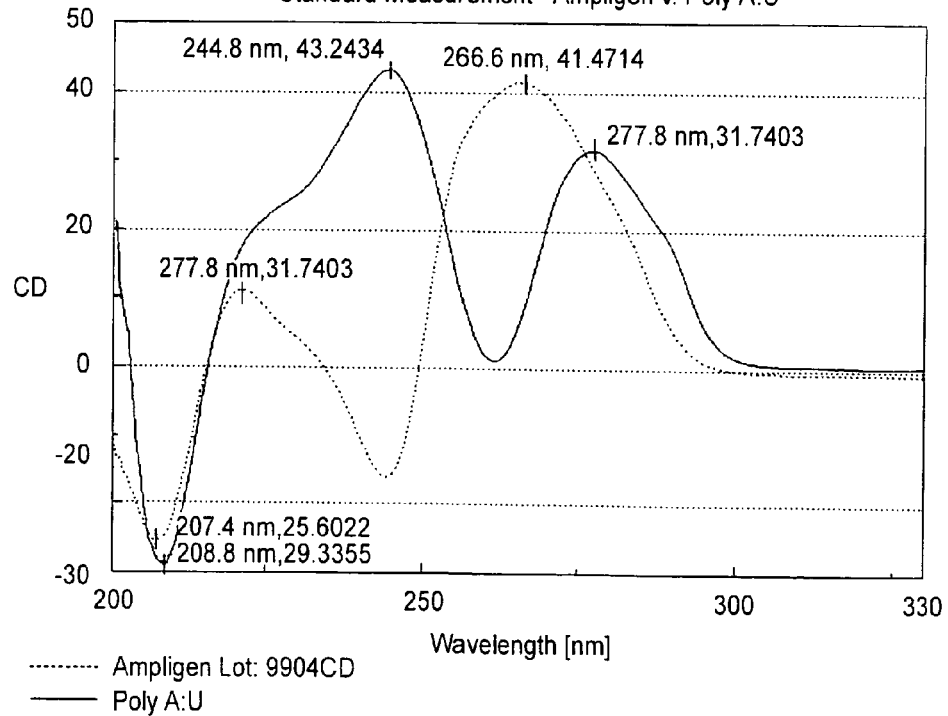
FIG. 14 shows a CD wavelength scan of poly (I):poly ($C_{12}U$) and poly(A):poly(U). A very weak and shifted single structure may be associated with the propensity for chiral aggregation of poly(A): poly(U)
Figure 15:
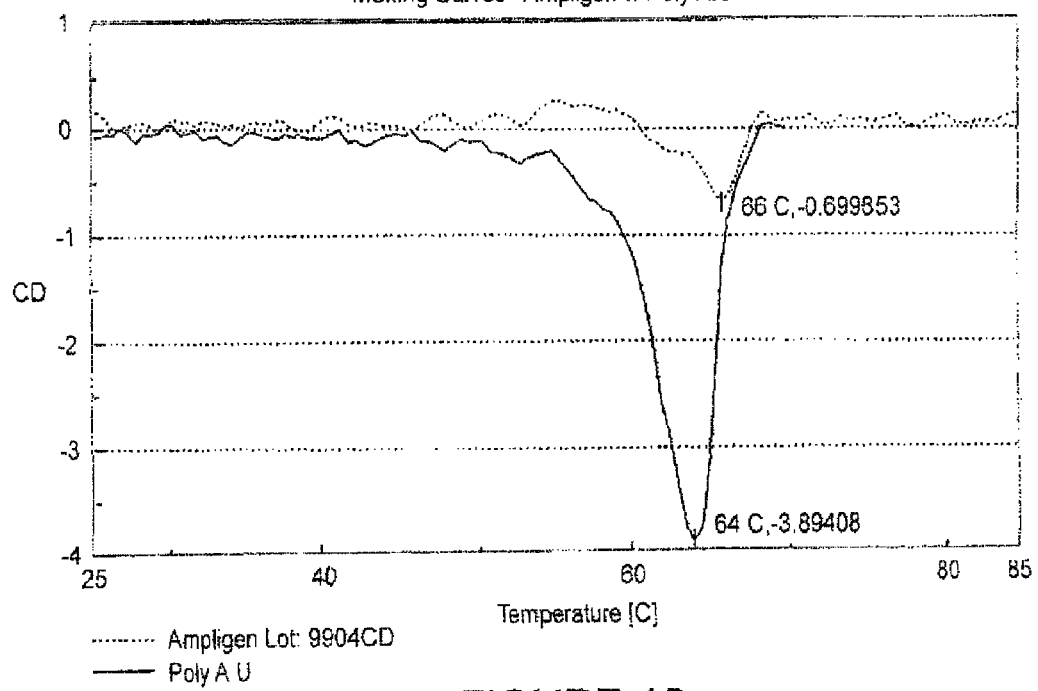
FIG. 15 shows a plot of the derivative of the thermal melt of poly(I):poly($C_{12}U$) and poly(A):poly(U). Somewhat high melting point is likely related to the aggregation tendency of poly(A):poly(U) noted in FIG. 14.
Figure 16:
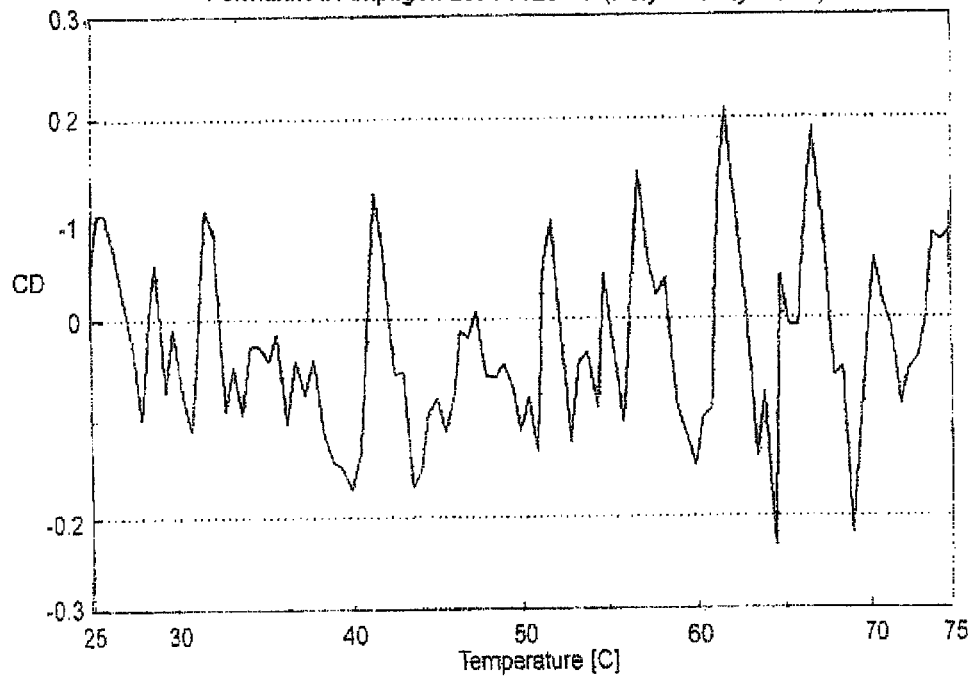
FIG. 16 shows the derivative of a thermal melt of single stranded poly (I):poly($C_{10}U$). The greater degree of Uridine substitution (compare poly(I):poly($C_{12}U$, FIG. 6) has compromised the double helical structure. The 1:12 ratio of U:C is optimal, providing one interruption per helical turn.
Figure 17:
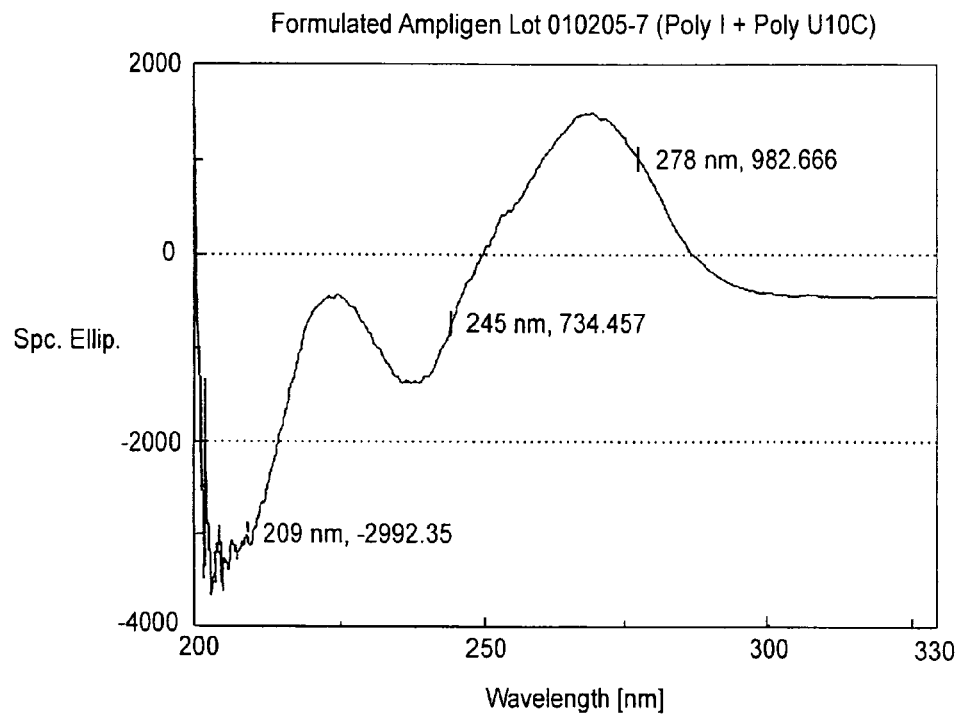
FIG. 17 shows a CD plot of thermal melt of single stranded poly (I):poly($C_{10}U$). Consistent with the lack of thermal melt behavior (FIG. 16), the greater degree of Uridine substitution (1:10 ratio of U:C, cf. 1:12 in poly(I):poly($C_{12}U$) has abolished the base stacking signal at 245 nm.

(a) Double-stranded ribonucleic acids of different nucleotide base composition, such as poly(I):poly($C_{12}U$), poly(I):poly(C), and poly(A):poly(U). (FIGS. 10, 12 and 14).

(b) Ampligen® poly(I):poly($C_{12}U$) that meets the polymer size specification.

(c) Double-stranded ribonucleic acid formulated from poly(I) and poly($C_xU_y$) strands with a cytidine to uridine base ratio of 11-14 to 1 (FIGS. 16 and 17) (C:U ratio=11:1 to 14:1).

The specificity of assays for dsRNA that differed in their nucleotide base composition was evidenced by comparison of CD scans and melting curves of similar, but different, double-stranded molecules, such as poly(I):poly($C_{12}U$), poly(I):poly(C), and poly(A):poly(U). CD scanning profiles appear to be similar, as seen with the scans of Ampligen®poly(I):poly($C_{12}U$) and poly(I):poly(C). But calculations of the ratios obtained at 278 nm and 245 nm, and subsequent t-test statistical analysis for equal means showed that the CD scan of Ampligen® differs significantly from similar dsRNA having different nucleotide base compositions. Specificity for the dsRNA of different nucleic acid base composition was also demonstrated by their thermal melting curves. Thermal melt curves for dsRNA differed significantly from each other. Statistical analysis (t-test for equal means) of data from the plots of the first derivative of the melting curves confirmed that the results obtained for their respective $T_M$ and width at half-height are significantly different. Therefore, specificity of the CD method differentiates Ampligen® from other dsRNA mole-cubes by parameters of both the scan and the thermal melt profiles.

The CD method is specific for detection of poly(I):poly($C_{12}U$) formulated from polymers not meeting the aforementioned specifications for size. When one or both polymers of the poly(I):poly($C_{12}U$) molecule is outside the 4-8S size specification, the results from the CD analysis of these molecules do not meet specifications for Ampligen® in regards to $T_M$ and width at half-height of the first derivative of the thermal melt curve. The failure to meet specifications for these CD parameters is observed with these formulations even when the ±1.5S size differential specification is satisfied. Relative to the data obtained from the thermal melt analyses of Ampligen® formulations, the $CD_{278}/CD_{245}$ ratio determinations were less specific. CD scans alone did not differentiate between poly(I):poly($C_{12}U$) and non-poly(I):poly($C_{12}U$) formulations that did not meet manufacturing and/or release specifications for polymer size.

As discussed above, the specificity of CD analysis is sensitive to the size of the single-stranded polymer strands. In addition, when the size difference between the complementary single-stranded polymer components, poly(I) and poly($C_{12}U$), is 2.4S or greater, the CD thermal melt analyses will differentiate poly(I):poly($C_{12}U$) from similar molecules not meeting the specification for the complementary polymer size differential.

CD analysis can distinguish between poly(I):poly($C_{12}U$) and similar mole-cubes that do not meet specifications for the amount of double strandedness or base pairing between the complementary poly(I) and poly($C_{12}U$) strands. The amount of base pairing is dependent on the relative proportion of cytidylic acid to uridylic acid (C:U ratio) of the poly($C_xU_y$) polymer. The ratio of cytidine to uridine in the poly($C_xU_y$) polymer affects the melting temperature ($T_M$) as well as the width at half height of the first derivative of the melting curve. When the ratio of cytidine to uridine is less than 11:1, there is less double strandedness or base pairing (between polyinosinic acid and polycytidylic acid complementary strands of the duplex RNA helix) than that for Ampligen®. This results in lower observed $T_M$'s and larger widths at half-height for the first derivative of the thermal melt curves relative to those observed for poly(I): poly($C_{12}U$). Increasing the cytidine to uridine ratio of the poly($C_xU_y$) strand increases the base pairing between the complementary strands of the helix and, therefore, increases the observed $T_M$ and decreases the observed width at half-height of the first derivative of the thermal curve. The $CD_{278}/CD_{245}$ ratio determinations were demonstrated to be less sensitive to differences in the C:U ratio in Ampligen® formulations.

Both the size of the complementary polymer strands and the C:U ratio of the poly($C_{12}U$) strand contribute to double strandedness of a poly(I):poly($C_{12}U$) molecule. The double strandedness, in turn, contributes to the efficacy of the drug product as discussed in the introduction. Therefore, CD method is an important analytical tool for characterization of poly(I):poly($C_{12}U$). Although CD scans and determinations of the $CD_{278}/CD_{245}$ ratio are less specific than the thermal melt analysis determinations of $T_M$ and width at half-height of the first derivative of the melt curve, all three CD parameters may be used in combination for the thorough characterization and identification of poly(I):poly($C_{12}U$).

Bioactivity and Stability of Rugged dsRNA

Bioactivity of dsRNA and poly(I):poly($C_{12}U$) were measured, and then compared utilizing a ligand-binding assay. Stability was measured using the product release test, reverse phase HPLC assay.

A summary of the results is presented below, followed by more detailed discussion. The combination of enhanced bioactivity and much greater stability under the thermal stress of 40° C. illustrate the "ruggedness" of this novel variant dsRNA (i.e., Rugged dsRNA) and suggest that it will be more bioavailable than most of the dsRNA molecules in a formulation of Ampligen®.

1. Bioactivity of Rugged dsRNA shows two-fold greater binding affinity as compared to unselected dsRNA Rugged dsRNA binding sites become unsaturated at a ratio of 0.50:1 (TLR3: Rugged dsRNA) or higher. But binding sites for Ampligen® poly(I): poly($C_{12}U$) become unsaturated at a ratio of 0.20:1 (TLR3: unselected dsRNA) or higher.

2. Stability of Rugged dsRNA is four-fold greater than unselected dsRNA

Ampligen® poly(I): poly($C_{12}U$) is stable (i.e., $S_{w,20}$>10.0) for less than 90 days when subjected to hydrolysis under thermal stress of 40° C. By contrast, Rugged dsRNA is stable for greater than 360 days under the same conditions. Rugged dsRNA also has an increased resistance to ribonuclease digestion.

3. Stability and bioactivity data show that Rugged dsRNA is more bioavailable than unselected dsRNA From these stability and bioactivity considerations, Rugged dsRNA is more bio-available for the relevant signaling receptor that conveys the therapeutic benefit. The Rugged dsRNA has the additional benefit of maintaining long-term stability at ambient temperatures, which has important clinical implications for treating populations in regions of the world without adequate refrigeration capabilities.

Bioactivity Background

Toll-like receptors (TLR) are signaling molecules recognizing pathogen-associated molecular patterns (PAMP) and activating innate immune defense mechanisms. TLR3 recognizes dsRNA, the genomic structure of some viruses, and also an intermediate generated during viral RNA replication. dsRNA is also produced intracellularly by stem-loop forming or with siRNA-aligned mRNAs. Ampligen® is comprised of dsRNA molecules that act through TLR3 binding and downstream signaling events. While poly(I):poly(C) signaling has alternate routes, the poly(I):poly($C_{12}$U) pathway acts exclusively through TLR3 binding as Ampligen® treatment protects TLR3$^{+/+}$ but not TLR3$^{-/-}$ mice from Punta Toro virus infection. TLR3$^{-/-}$ cells do not produce IFN upon poly(I):poly($C_{12}$U) treatment while IFN is induced by poly (I):poly(C) in TLR3 knockout cells.

The TLR3 molecule ectodomain (ECD) conformation and its relation to binding of dsRNA is well characterized, including the prospective binding site. Amino acids H539 and N541 are involved in the interaction with the double helix. Mutational analysis of these amino acids at the binding site further strengthens the argument.

The effect of length and structure of dsRNA on TLR3 binding and IFN induction is known. Inosine$_{30}$ ($I_{30}$):poly(C) or poly(I):Cytosine$_{30}$ ($C_{30}$) induced interferon (IFN), but shorter dsRNA stretches do not induce IFN. Compared to them, however, IFN induction by poly(I):poly(C) was always superior. $I_{20}$:$C_{20}$, $I_{30}$:$C_{30}$, and $I_{40}$:$C_{40}$ were ineffective IFN inducers. Therefore, characterizing Ampligen® by its TLR3 binding capacity is a biomarker to predict its biological activity.

Bioactivity Method

A range of ratios of TLR3-ECD to unselected Ampligen® or Rugged dsRNA are reacted by the method of Leonard (2008). The components are separated by the size-exclusion chromatographic method described below. From the peak quantities of free TLR3-ECD and the ligand-receptor complex, the ratio of TLR3-ECD that is required for saturation of either Ampligen® or Rugged dsRNA is determined. This threshold TLR3-ECD/dsRNA ratio provides a direct indication of the strength of the ligand-receptor binding and, therefore, of bioactivity.

The following method is an adaptation of the experimental procedures used to characterize TLR3 ligand binding at a molecular level. Since TLR3-ECD (1.12×10$^2$ Kda) and poly(I):poly($C_{12}$U) (0.2–2×10$^3$ Kda) have different elution patterns, they can be separated from each other by size-exclusion chromatography (SEC). According to results obtained from poly(I):poly(C) using a SUPERDEX 200 PC 3.2/30 column and collecting 80 μl fractions, most of the poly(I):poly(C) appears in fractions 3-5 while TLR3-ECD is eluted in fractions 9-12 (Bell, 2005).

The binding of TLR3-ECD to poly(I):poly(C) or poly(I):poly($C_{12}$U) creates a complex that is larger in size than either of the initial components. The later eluting free TLR3-ECD is separated from the complex. Optimization of the separation identified that the SUPEROSE 200 PC column afforded superior binding by reducing tailing, due to absence of nonspecific interactions with dsRNA.

Figure 18A:
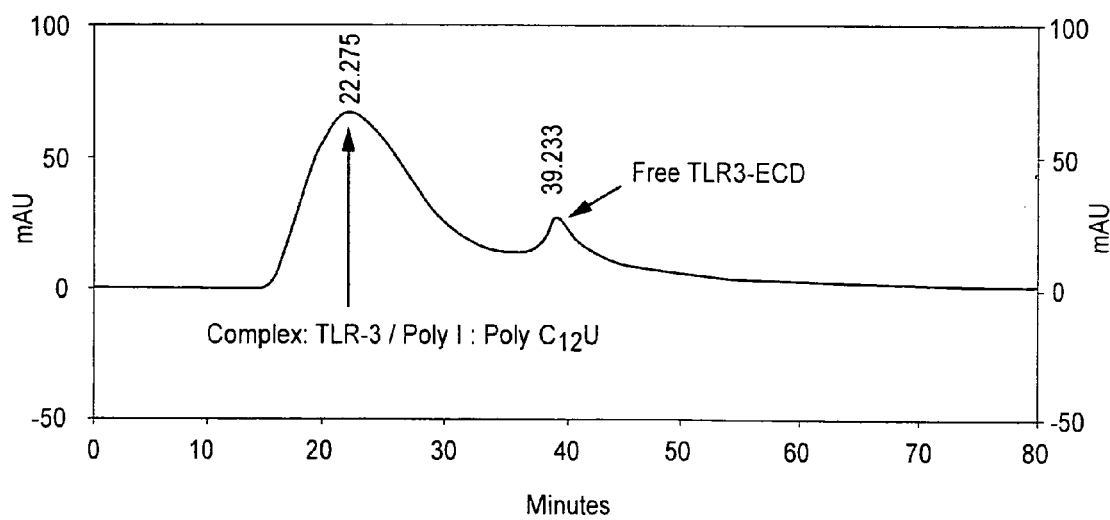
FIG. 18 shows size exclusion chromatography of complexes of TLR3-ECD and poly(I):poly($C_{12}U$) (FIG. 18A), the receptor TLR3-ECD only (FIG. 18B), and the ligand poly(I):poly($C_{12}U$) only (FIG. 18C).
Figure 18B:
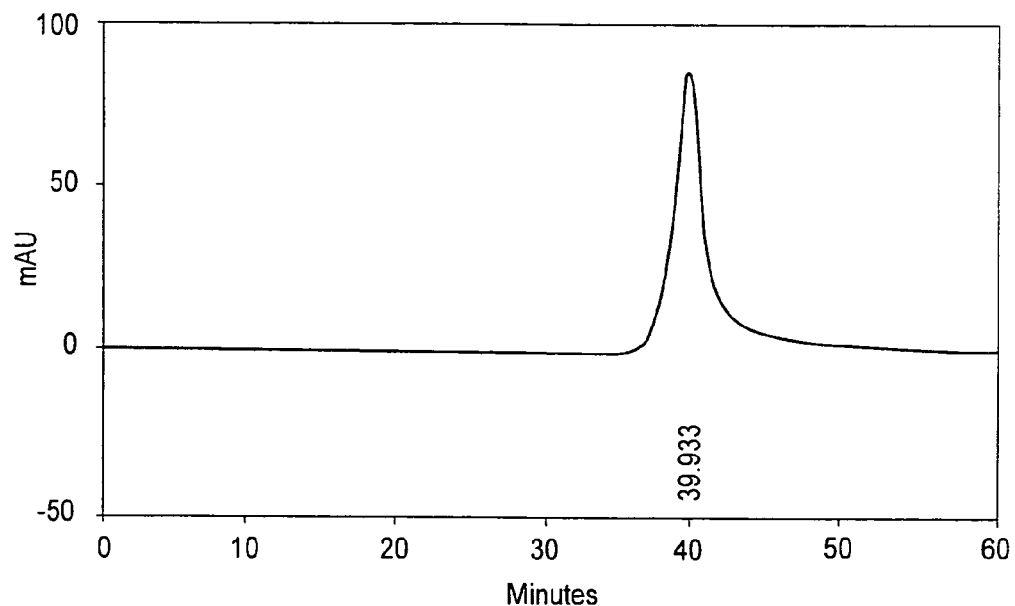
Figure 18C:
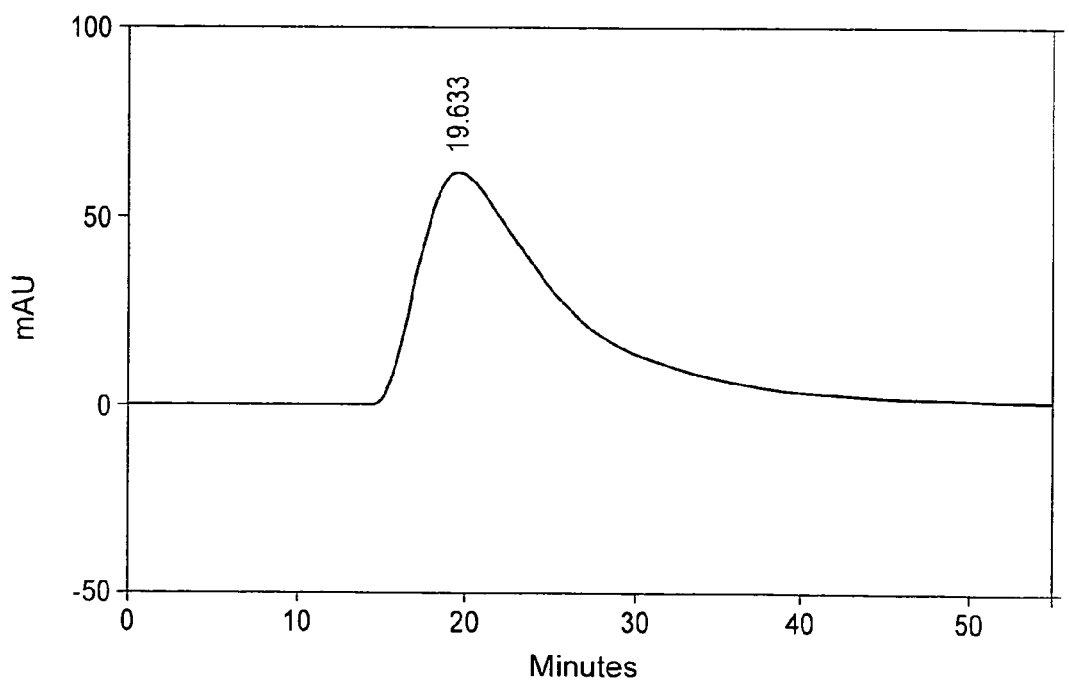

FIG. 18 shows the resulting chromatograms obtained from the reacted mixture of TLR3-ECD/poly(I):poly($C_{12}$U) compared to component injections of TLR3-ECD and poly(I):poly($C_{12}$U) alone, respectively.

Characterization of Peaks.

Identification and quantitation of TLR3-ECD in size-exclusion chromatography fractions is possible in an ELISA format. The commercially-available TLR3-ECD is a His tag-containing recombinant protein. A capture anti-His tag antibody immobilizes TLR3-ECD in a microplate well. A second, biotinylated primary antibody quantitatively binds to the immobilized TLR3-ECD. This secondary antibody is selected to have an epitope distal from the dsRNA binding site on the TLR3-ECD molecule and also from the epitope recognized by the capture antibody. HRP-conjugated streptavidin recognizes the biotinylated second primary antibody. The appropriate substrate metabolized by HRP produces a soluble color suitable for quantitative measurement of TLR3-ECD.

Ampligen® concentration in the size-exclusion chromatography fractions is measured by fluorescence using standard dilutions and chromatography fractions in a quantitative riboGreen test. This assay permits testing of Ampligen® out-of-the-bottle (i.e., not selected for Rugged dsRNA) without further processing, preparation, or extraction, thereby maintaining its condition as a pharmaceutical.

Bioactivity Results.

Results in Table 6 show the percentage of free TLR3-ECD that remains in a series of reactions using different ratios of TLR3-ECD to dsRNA. These studies were conducted with either unimproved Ampligen® as well as Rugged dsRNA.

Binding of TLR3-ECD to Rugged dsRNA is more effective than binding of TLR3-ECD to unimproved Ampligen®. An approximately 2-fold greater ratio of TLR3-ECD is required to "unsaturate" Rugged dsRNA (~0.50:1) as compared to Ampligen® (0.25:1). Also, the binding profile at various ratios shows a much sharper endpoint for saturation for the case of Rugged dsRNA which may reflect greater structural uniformity for this more compact dsRNA.Table 6. Bioactivity Measurements of Unimproved Ampligen® vs. Rugged dsRNA.

| Molar Ratio of TLR3 to dsRNA | Unimproved/Old Ampligen ®, Lot # 0701HE | | New Rugged dsRNA | |
|---|---|---|---|---|
| | dsRNA/TLR3 Complex Area % | Free TLR3 Area % | dsRNA/TLR3 Complex Area % | Free TLR3 Area % |
| 0.20:1 | 99.0 | 0.978 | 99.4 | 0.577 |
| 0.25:1 | 78.4 | 21.6 | 99.1 | 0.880 |
| 0.33:1 | 20.9 | 79.1 | 92.9 | 7.086 |
| 0.50:1 | 58.9 | 41.1 | 60.3 | 39.723 |
| 0.67:1 | 15.4 | 84.6 | 11.3 | 88.660 |

The TLR3 binding of Rugged dsRNA is 100% superior in receptor binding than the unimproved/old Ampligen® preparation. As shown in Table 6, Free TLR3 (area >10%) appears at a TLR3:dsRNA ratio of 0.25:1 for unimproved Ampligen® as compared to a 0.50:1 for Rugged dsRNA Stability of Rugged dsRNA.

Figure 19:
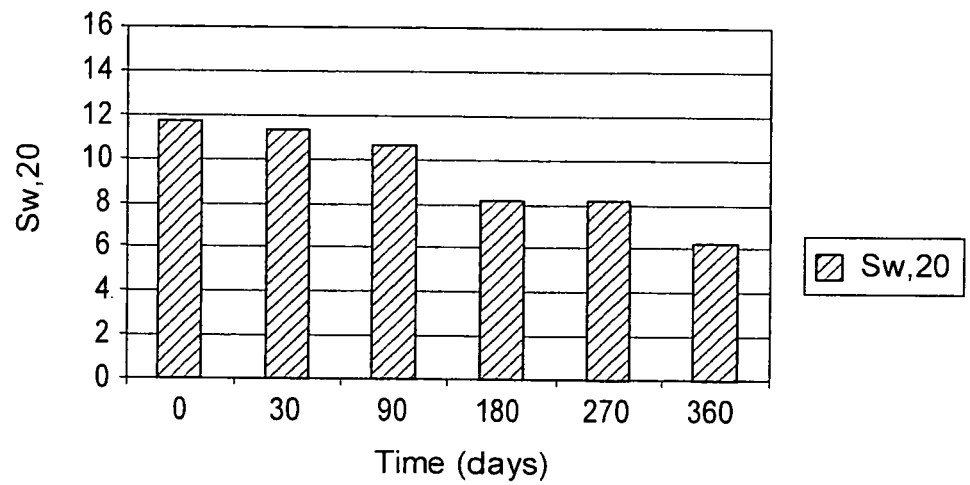
FIG. 19 shows the effect of thermal stress (40° C.) on the size of dsRNA as measured by analytical centrifugation. The decrease in sedimentation coefficient ($S_{20,w}$) reflects a loss of size due to hydrolysis.

Stability of poly(I):poly($C_{12}$U) was measured at an accelerated temperature condition of 40° C. as compared to the long-term storage temperature of from 2° C. to 8° C. As shown in FIG. 19, the size of poly(I): poly($C_{12}$U) decays at this temperature as measured by analytical ultracentrifugation ($S_{20,w}$). Decrease in size is due to unfolding of the double helix (loss of hydrogen bonds) and concurrent hydrolysis of the phosphodiester bonds. For bioactivity unimproved Ampligen® (poly(I):poly($C_{12}$U) requires a sedimentation coefficient from about 10.0 to about 15.0 $S_{(20,w)}$, whereas the size of poly(I):poly($C_{12}$U) at more than 180 days is about 8.0 $S_{(20,w)}$ and indicates a loss of bioactivity.

Figure 20:
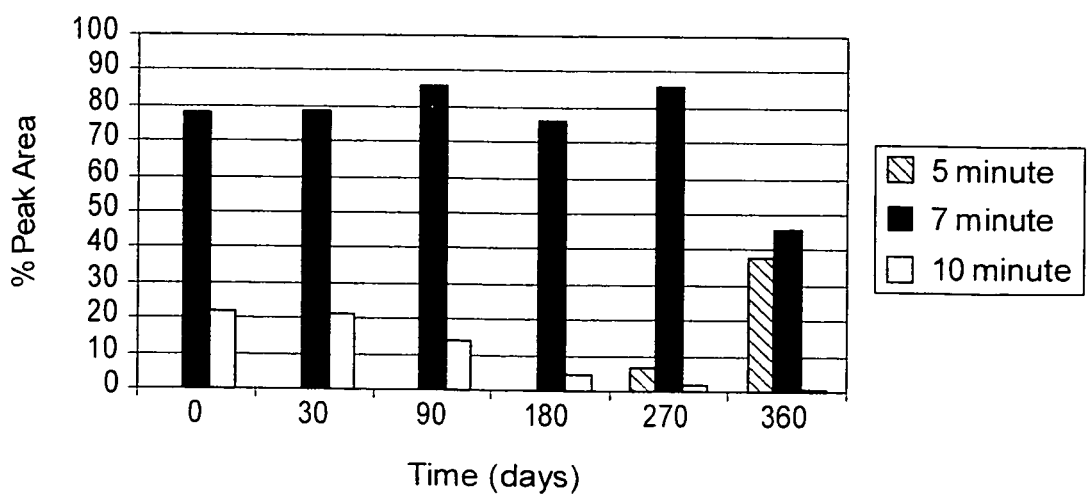
FIG. 20 shows the effect of thermal stress (40° C.) upon the component strands of dsRNA (7 minute and 10 minute peaks) and the Rugged dsRNA as measured by high performance liquid chromatography (HPLC). Whereas the larger poly(I) and poly($C_{12}U$) strands hydrolyze at 40° C., the quantity of Rugged dsRNA peak increases.

FIG. 20 shows the results of a second stability indicating parameter, the reversed phase HPLC assay, previously described; that separates poly(I): poly($C_{12}$U) into its individual strands (7 minute and 10 minute peaks). It is clearly evident that hydrolysis begins with the poly(I) strand (10 minute peak) followed by the poly($C_{12}$U) strand (7 minute peak). HPLC results show that loss of size does not begin until commencement of the hydrolysis of the second strand poly($C_{12}$U); the RNA molecule retains double-stranded structure when only one of the strands undergoes hydrolysis. This loss of size at about 90 days occurs with the hydrolysis of both poly(I) and poly($C_{12}$U) strands.

Importantly, the Rugged dsRNA (5 min) peak is entirely unaffected by thermal stress. In fact, it increases in relation to the poly(I) and poly($C_{12}$U) strands. This conclusively shows that Rugged dsRNA is not only "rugged" but can form spontaneously from smaller strands of degraded poly(I):poly($C_{12}$U).

Structure of Novel Improved Rugged dsRNA Compared to Old Unimproved Ampligen® Mixture Transmission Electron Microscopy (TEM) was used to compare the structure of the new improved Rugged dsRNA vs. the old unimproved Ampligen® mixture of dsRNA molecules. As shown in FIGS. 26, 27, and 28 the unimproved Ampligen® mixture contains molecules with a high degree of branching compared to the new improved Rugged dsRNA (FIG. 29). In fact the majority of molecules in the Ampligen® mixture are branching, while the majority of dsRNA molecules in the improved Rugged dsRNA are unbranched. Also, the unimproved Ampligen® mixture contains 4-5 times more molecules with 3 or more branches than the new improved Rugged dsRNA. Therefore, not only does Rugged dsRNA contain a higher percentage of non-branched molecules, the small percentage of branched molecules present contain primarily a single branch as compared to the unimproved Ampligen® mixture which contains many more highly branched variant molecules with >3 branched strands. The binding affinity of dsRNA to TLR3 is a function of the length of the linear non-branched dsRNA. This explains the increased bioactivity of Rugged dsRNA compared to the old unimproved Ampligen® mixture.

Patents, patent applications, books, and other publications and information sources cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

REFERENCES

Alexopoulou L, Holt A C, Medizhitov R & Flavell R (2001) Recognition of double-stranded RNA activation and of NF-$_κ$B by Toll-like receptor 3. Nature 413, 732-738.

Bell J K, Botos I, Hall P R, Askins J, Shiloach J, Segal DM & Davies DR (2005) The molecular structure of the Toll-like receptor 3 ligand-binding domain. Proc. Natl. Acad. Sci. USA 102, 10976-10980.

Bell J K, Askins J, Hall P R, Davies D R & Segal D M (2006) The dsRNA binding site of human Toll-like receptor 3. Proc. Natl. Acad. Sci, USA 103, 8792-8797.

Brodsky I & Strayer D R (1987) Therapeutic potential of Ampligen. Am. Fam. Physician 36, 253-256.

Brown B A, Athanasiadis A, Hanlon E B, Lowenhaupt K, Wilbert C M & Rich A (2002) Crystallization of the Zα domain of the human editing enzyme ADAR1 complexed with a DNA-RNA chimeric oligonucleotide in the left-handed Z-conformation. Acta Cryst. D58, 120-123.

Choe J, Kelker M S & Wilson I (2005) Crystal structure of Toll-like receptor 3 (TLR3) ectodomain. Science 309, 581-585.

Ghazaryan A A, Dalyan Y B, Haroutiunian S G, Tikhomirova A, Taulier N, Wells J W & Chlikian T V (2006) Thermodynamics of interations of water-soluble porphyrins with RNA duplexes. J. Am. Chem. Soc. 128, 1914-1921.

Gowen B B, Wong M H, Jung K H, Sanders A B, Mitchell W M, Alexopoulou L, Flavell R A & Sidwell R W (2007) TLR-3 is essential for the induction of protective immunity against Punta Toro virus infection by the double-stranded RNA (dsRNA), poly (I:$C_{12}$U), but not poly (I:C): Differential recognition of synthetic dsRNA molecules. J. Immunol. 178, 5200-5208.

Gray D M, Hung S & Johnson K H (1995) Absorption and circular dichroism spectroscopy of nucleic acid duplexes and triplexes. Meth. Enzymol. 246, 19-34.

Greene J J, Ts'o P O, Strayer D R & Carter W A (1984) Therapeutic applications of double-stranded RNAs. In: *Interferons and Their Applications* (Came P E & Carter W A, eds), Springer Verlag, Chapter 26.

Leonard J N, Ghirlando R, Askins J, Bell J K, Margulies D H, Davies D R & Segal D M (2008) The TLR3 signaling complex forms by cooperative receptor dimerization. Proc. Natl. Acad. Sci. USA 105, 258-263.

Lesnik E A & Freier S M (1995) Relative thermodynamic stability of DNA, RNA and DNA: RNA hybrid duplexes: Relationship with base composition and structure. Biochemistry, 34, 10807-10815.

Liu L, Botos I, Wang Y, Leonard J N, Shiloach J, Segal D M, Davies D R. Structural basis of toll-like receptor 3 signaling with double-stranded RNA. Science. 2008; 320:379-381.

Pichlmair A, Schulz 0, Tan C P, Naslund T I, Liljestrom P, Weber F & Reise e Sousa C (2006) RIG-1-mediated antiviral responses to single-stranded RNA bearing 5'-phosphates. Science 314, 997-1000.

Schroeder M & Bowie A G (2005) TLR3 in antiviral immunity: Key player or bystander? Trends Immunol. 26, 462-468.

Sorrentino S, Naddeo M, Russo A & Alessio G D (2003) Degradation of double-stranded RNA by human pancreatic ribonuclease: Crucial role of noncatalytic basic amino acid residues. Biochemistry 42, 10182-10190.

Sumita M, DeSaulnier J P, Chan Y C, Chui H M P, Clos L & Chow CS (2005) Effects of nucleotide substitution and modification on the stability and structure of helix 69 from 28S rRNA. RNA 11, 1420-1429.

What is claimed is:

1. An isolated double-stranded ribonucleic acid (dsRNA) which is resistant to denaturation under conditions that are able to separate hybridized poly(riboinosinic acid) and poly (ribocytosinic acid) strands, wherein only a single strand of said isolated dsRNA comprises one or more uracil or guanine bases that are not base paired to an opposite strand and wherein said single strand is comprised of poly (ribocytosinic$_{30-35}$uracilic acid).

2. The isolated dsRNA of claim 1, wherein said single strand is partially hybridized to an opposite strand comprised of poly(riboinosinic acid).

3. An isolated double-stranded ribonucleic acid (dsRNA) which is resistant to denaturation under conditions that are able to separate hybridized poly(riboinosinic acid) and poly (ribocytosinic acid) strands, wherein said isolated dsRNA is comprised of ribo($I_n$).ribo($C_{30-35}U$)$_n$, in which ribo is a ribonucleotide and n is an integer from 40 to 500.

4. The isolated dsRNA of claim 3, wherein said isolated dsRNA is comprised of ribo($I_n$).ribo($C_{30}U$)$_n$, in which ribo is a ribonucleotide and n is an integer from 40 to 500.

* * * * *

UNITED STATES PATENT AND TRADEMARK OFFICE
CERTIFICATE OF CORRECTION

PATENT NO. : 8,722,874 B2  
APPLICATION NO. : 13/077742  
DATED : May 13, 2014  
INVENTOR(S) : Carter et al.

It is certified that error appears in the above-identified patent and that said Letters Patent is hereby corrected as shown below:

IN THE CLAIMS:

Claim 1, column 30, line 13, change poly(ribocytosinic acid) to -- poly(ribocytidylic acid) --.

Claim 1, column 30, lines 16-17, change poly(ribocytosinic$_{30-35}$uracilic acid) to -- poly(ribocytidylic$_{30-35}$uridylic acid) --.

Claim 3, column 30, line 24, change poly(ribocytosinic acid) to -- poly(ribocytidylic acid) --.

Claim 3, column 30, line 25, change ribo(I$_n$).ribo(C$_{30-35}$U)$_n$ to -- ribo(I$_n$)•ribo(C$_{30-35}$U)$_n$ --.

Claim 4, column 30, line 28, change ribo(I$_n$).ribo(C$_{30}$U)$_n$ to -- ribo(I$_n$)•ribo(C$_{30}$U)$_n$ --.

Signed and Sealed this  
Twelfth Day of August, 2014

Michelle K. Lee  
*Deputy Director of the United States Patent and Trademark Office*